United States Patent
McMorris et al.

(10) Patent No.: US 6,639,105 B2
(45) Date of Patent: *Oct. 28, 2003

(54) ILLUDIN ANALOGS USEFUL AS ANTITUMOR AGENTS

(75) Inventors: Trevor C. McMorris, LaJolla, CA (US); Michael J. Kelner, LaJolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/134,260

(22) Filed: Apr. 29, 2002

(65) Prior Publication Data

US 2002/0161206 A1 Oct. 31, 2002

Related U.S. Application Data

(60) Continuation of application No. 09/501,151, filed on Feb. 9, 2000, now Pat. No. 6,380,403, which is a continuation of application No. 09/241,172, filed on Feb. 1, 1999, now Pat. No. 6,069,283, which is a division of application No. 08/683,687, filed on Jul. 18, 1996, now Pat. No. 5,932,553.

(51) Int. Cl.[7] ...................... C07C 229/52; C07D 493/10

(52) U.S. Cl. ........................ 562/553; 562/556; 568/374; 549/330

(58) Field of Search .......................... 549/330; 562/553, 562/556; 568/374

(56) References Cited

U.S. PATENT DOCUMENTS

| | | | |
|---|---|---|---|
| 4,559,157 A | 12/1985 | Smith et al. | 252/90 |
| 4,608,392 A | 8/1986 | Jacquet et al. | 514/844 |
| 4,612,302 A | 9/1986 | Szabo et al. | 514/11 |
| 4,684,620 A | 8/1987 | Hruby et al. | 514/11 |

(List continued on next page.)

FOREIGN PATENT DOCUMENTS

| | | |
|---|---|---|
| JP | 62-234040 | 10/1987 |
| WO | WO-91/04754 | 4/1991 |
| WO | WO-94/18151 | 8/1994 |

(List continued on next page.)

OTHER PUBLICATIONS

Curtis, Erin.A. ,et al. ,"An Efficient Dipolar–Cycloaddition Route to the Pterosin Family of Sesquiterpenes", *Tetrahedron Letters*, 36 (*12*) , (Mar. 1995),pp. 1989–1992.

Dillman, R..O. ,et al. , "Athymic Mouse Model of a Human T–Cell Tumor", *Cancer Research*, 45, (Nov. 1985),pp. 5632–5636.

French, A..L. ,et al. , "Poisoning with the North American Jack O'Lantern Mushroom", *Clinical Toxicology*, 26 (*1* &*2*), (1988),pp. 81–88.

Kelner, M..J. ,et al. ,"Preclinical Evaluation of Illudens as Anticancer Agents", *Cancer Research*, 47, (1987),pp. 3186–3189.

Tanaka, Ken.,et al. ,"Michael–type addition of illudin S, a toxic substance from *Lampteromyces japonicus* with Cysteine and Cysteine–containing peptides in vitro", *Chem. Pharm. Bull.*, vol. 44, No. 2, (1996),pp. 273–279.

Anchel, Marjorie.,et al. , "Antibiotic Substances From Basidiomycetes. VII. Clitocybe Illudens", *Proceedings of the National Academy of Sciences*, 36 (5), (1950),pp. 300–305.

Anchel, M..,et al. , "The Biogenesis of Illudins S and M in Clitocybe Illudens",*Phytochemistry, 9 (11)*, (Nov. 1970),pp. 2339–2343.

Arap, W..,et al. , "Cancer Treatment by Targeted Drug Delivery to Tumor Vasculature in a Mouse Model", *Science*, 279, (Jan. 16, 1998),pp. 377–380.

Brandsteterova, E..,et al. , "HPLC Analysis of Novel Anti-–Cancer Agents–Illudens and Their Analogs", *Journal of Liquid Chromatography*, 16 (*1*), (1993),pp. 115–125.

Brandsteterova, E..,et al. , "HPLC Determination of a New Anticancer Agent (Acylfulvene) in Serum", *Neoplasma, 39 (6)*, (1992),pp. 369–373.

Burres, N..S. , et al. , "Antitumor Activity and Mechanism of Action of the Novel Marine Natural Products Mycalamide–A and –B and Onnamide", *Cancer Research*, 49, (Jun. 1989),pp. 2935–2940.

(List continued on next page.)

(57) ABSTRACT

The present invention provides illudin analogs of the general formula (I):

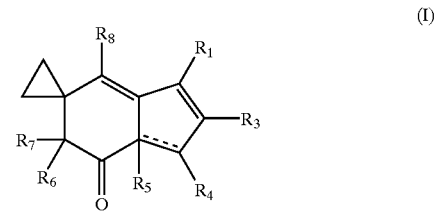

(I)

where $R_1$ is $(CH_2)_n$—X—Y or H; n is 0 to 4; X is O or S or N or absent; and Y is an optionally substituted $(C_1-C_8)$alkyl, $(C_6-C_{10})$aryl, $(C_6-C_{10})$aryl$(C_1-C_4)$alkyl or cyclo$(C_3-C_6)$ alkyl optionally comprising one or more heteroatoms; a monosaccharide, an amino acid residue, or H when n is 2–4;

$R_2$ is absent; or $R_1$ and $R_2$ together comprise a 5–7 membered cyclic ring;

$R_3$ is $(C_1-C_4)$alkyl or H; $R_4$ is H, $SCH_2CO_2$ $(C_1-C_4)$alkyl, O—$(C_5-C_{12})$aryl or —S—$(C_5-C_{12})$aryl; $R_5$ is H, OH or absent; $R_6$ is $(C_1-C_4)$alkyl or absent; $R_7$ is OH or $OSi((C_1-C_4)alkyl)_3$; or $R_6$ and $R_7$ together are ethylenedioxy;

$R_8$ is optionally substituted $(C_1-C_4)$alkyl; and the bonds represented by—are individually present or absent. The invention further provides dimers comprising analogs of formula (I).

7 Claims, 7 Drawing Sheets

U.S. PATENT DOCUMENTS

| | | | |
|---|---|---|---|
| 4,820,508 A | 4/1989 | Wortzman | 424/59 |
| 4,853,371 A | 8/1989 | Coy et al. | 514/12 |
| 4,938,949 A | 7/1990 | Borch et al. | 424/10 |
| 4,992,478 A | 2/1991 | Geria | 514/782 |
| 5,387,578 A | 2/1995 | Angelucci et al. | 514/21 |
| 5,439,936 A | 8/1995 | Kelner et al. | 514/546 |
| 5,439,942 A | 8/1995 | Kelner et al. | 514/691 |
| 5,523,490 A | 6/1996 | Kelner et al. | 568/374 |
| 5,563,176 A | 10/1996 | Kelner et al. | 514/691 |
| 5,723,632 A | 3/1998 | McMorris | 549/331 |
| 5,932,553 A | 8/1999 | McMorris et al. | 514/23 |
| 6,025,328 A | 2/2000 | McMorris et al. | 514/2 |

FOREIGN PATENT DOCUMENTS

| | | |
|---|---|---|
| WO | WO-94/25013 | 11/1994 |
| WO | WO-96/34005 | 10/1996 |
| WO | WO-97/03995 | 2/1997 |
| WO | WO-98/03458 | 1/1998 |

OTHER PUBLICATIONS

Eva, K..M. , et al. , "An Efficient Synthesis of Pterosin C and Other Pterosins", *Canadian Journal of Chemistry, 62 (10)*, (Oct. 1984),pp. 1945–1953.

Giovanella, B..C. ,et al., "Correlation Between Response to Chemotherapy of Human Tumors in Patients and in Nude Mice", *Cancer, 52*, (1983),pp. 1146–1152.

Giovanella, B..C. , et al., "DNA Topoisomerase I–Targeted Chemotherapy of Human Colon Cancer in Xenografts", *Science, 246 (4933)*, (Nov. 24, 1989),pp. 1046–1048.

Goldin, A..,et al., "Current Results of the Screening Program at the Division of Cancer treatment, National Cancer Institute", *Europ. J. Cancer, 17*, (1981),pp. 129–142.

Goldin, A..,et al., "Historical Development and Current Strategy of the National Cancer Institute Drug Development Program", *In: Methods in Cancer Research, vol. XVI, Cancer Drug Development Part A, Chapter V*, Academic Press, Inc., New York, (1979),pp. 165–245.

Greene, T..W. , *Protective Groups in Organic Synthesis, Chapters 4, 5 & 6*, John Wiley & Sons, Inc., New York, (1981),pp. 114–217.

Hanson, J..R., et al. , "Studies in Terpenoid Biosynthesis. Part XV. Biosynthesis of the Sesquiterpenoid Illuden M", *Journal of the Chemical Society, Perkin Transactions I*,(1976),pp. 876–880.

Hara, M..,et al. , "6–Deoxyilludin M, a New Antitumor Antibiotic: Fermentation, Isolation and Structural Identification", *The Journal of Antibiotics, 40*, (Nov. 1987),pp. 1643–1646.

Harttig, U..,et al. , "Leaianafulvene, a Sesquiterpenoid Fulvene Derivative from Cultures of Mycena Leaiana", *Phytochemistry, 29 (12)*, (1990),pp. 3942–3944.

Hirono, I..,et al. , "Reproduction of Acute Bracken Poisoning in a Calf with Ptaquiloside, a Bracken Constituent", *The Veterinary Record, 115 (15)*, (Oct. 1984),pp. 375–378.

Inoue, K..,et al. , "Antitumor Efficacy of Seventeen Anticancer Drugs in Human Breast Cancer Xenograft (MX–1) Transplanted in Nude Mice", *Cancer Chemother. Pharamacol., 10*, (1983),pp. 182–186.

Kawato, Y..et al. , "Antitumor Activity of a Camptothecin Derivative, CPT–11, Against Human Tumor Xenografts in Nude Mice", *Cancer Chemother. Pharmacol., 28*, (1991),pp. 192–198.

Kelner, M..J. ,et al., "In Vitro and In Vivo Studies on the Anticancer Activity of Dehydroilluden M", *Anticancer Research, 15*, (1995),pp. 873–878.

Kelner, M..J. ,et al., "Nonresponsiveness of the Metastatic Human Lung Carcinoma MV522 Xenograft to Conventional Anticancer Agents", *Anticancer Research, 15*, (1995),pp. 867–872.

Kelner, M..J. ,et al., "Preclinical Evaluation of Illudens as Anticancer Agents: Basis for Selective Cytotoxicity", *J. Natl. Cancer Inst., 82 (19)*, (1987),pp. 1562–1565.

Lu, Jianliang.,et al., "An expeditious synthesis of the potent antitumor agent, (+)–hydroxymethylacylfulvene using an allenic Paulson–Khand type cycloaddition", *American Chemical Society, Division of Organic Chemistry Abstracts*, 217th ACS National Meeting in Anaheim, CA,(Mar. 21–25, 1999), 1 p.

Matsumoto, Takeshi.,et al., "An Alternative Synthesis of Illudin M", *Tetrahedron Letters, 14*, (Mar. 1970),pp. 1171–1174.

Matsumoto, T..,et al. , "Synthesis of Illudin S", *Tetrahedron Letters, 23*, (May 1971),pp. 2049–2052.

McMorris, T..C.,et al., "(Hydroxymethyl) Acyfulvene: An Illuden Derivative with Superior Antitumor Properties", *Journal of Natural Products, 59 (9)*, (Sep. 1996),pp. 896–899.

McMorris, T..C. ,et al., "(Hydroxymethyl)acylfulvene: An Illudin Derivative with Superior Antitumor Properties", *Chemical Abstracts, abstract No. 196032*, vol. 125, No. 15,(Oct. 7, 1996).

McMorris, T..C. ,et al. , "Acylfulvenes, a New Class of Potent Antitumor Agents", *Experientia, 52 (1)*, (Apr. 21, 1995),pp. 75–80.

McMorris, Trevor.C. ,et al., "An Acetal Derivative of Illudin S with Improved Antitumor Activity", *Tetrahedron letters, 38 (10)*, (1997),pp. 1697–1698.

McMorris, Trevor.C. ,et al., "Design and Synthesis of Antitumor Acylfulvenes", *The Journal of Organic Chemistry 62 (9)*, (1997),pp. 3015–3018.

McMorris, T..C. ,et al. , "Fungal Metabolites. The Structures of the Novel Sesquiterpenoids Illudin –S and –M", *J. of Amer. Chem. Soc., 87 (7)*, (1965),pp. 1594–1600.

McMorris, T..C. ,et al., "On the Mechanism of Toxicity of Illudens: The Role of Glutathione", *Chemical Research Toxicology, 3 (6)*, (Nov./Dec. 1990),pp. 574–579.

McMorris, T..C. ,et al., "Reaction of Antitumor Hydroxymethylacylfulvene (HMAF) with Thiols", *Tetrahedron, 53 (43)*, (1997),pp. 14579–14590.

McMorris, T..C. , et al., "Structure and reactivity of Illudens", *Tetrahedron, 45 (17)*, (1989),pp. 5433–5440.

McMorris, T..C. , et al. , "Structure–Activity Relationships of Illudens: Analogs with Improved Therapeutic Index", *Journal of Organic Chemistry, 57 (25)*, (Dec. 4, 1992),pp. 6876–6883.

McMorris, Trevor.C. , et al. , "Total Synthesis of hydroxymethylacylfulvene, an antitumuor derivative of illudin S", *Chem. Commun.*, (1997),pp. 315–316.

Padwa, Albert.,et al., "An approach toward the Illudin family of sesquiterpenes using the tandem cyclization–cycloaddition reaction of rhodium carbenoids", *The Journal of Organic Chemistry, 62 (5)*, (Mar. 7, 1997),pp. 1317–1325.

Padwa, Albert., et al.,"Generation and Cycloaddition behavior of spirocyclic carbonyl ylides. Application to the synthesis of the Pterosin Family of Sequiterpenes", *The Journal of Organic Chemistry, 61 (1)*, (Jan. 12, 1996),pp. 73–81.

Padwa, Albert.,et al. , "Synthetic studies toward Illudins and Ptaguilosin. A Highly Convergent approach via the dipolar cycloaddition of carbonyl ylides", *The Journal of the American Chemical Society, 116*, (1994),pp. 2667–2668.

Schabel, F..M. , et al. , "Testing Therapeutic Hypotheses in Mice and Man:Observations on the Therapeutic Activity Against Advanced Solid Tumors of Mice Treated with Anticancer Drugs that Have Demonstrated or Potential Clinical Utility for Treatment of Advanced Solid Tumors of Man", *In: Methods in Cancer Research, vol. XVII, Cancer Drug Development Part B, Chapter 1*, Academic Press, Inc.,(1979),pp. 3–50.

Shimomura, O.., "The Role of Superoxide Dismutase in Regulating the Light Emission of Luminescent Fungi", *The Journal of Experimental Botany, 43 (256)*, (Nov. 1992),pp. 1519–1525.

Shinozawa, S..,et al. , "The Antitumor Effect of Illudin S (Lampterol) Entrapped in Liposome for Mice Inolculated with Ehrlich Ascites Tumor Cells", *Chemical Abstracts, 90 (25)*, Abstract No. 197682m,(Jun. 18, 1979), 1 p.

Steel, G..G.,et al., "The Response to Chemotheraphy of a Variety of Human Tumor Xenografts", *Br. J. Cancer, 47*, (1983),pp. 001–013.

Tanaka, K..,et al. ,"Metabolism by Rat Liver Cytosol of Illuden S, a Toxic Substance of Lampteromyces Japonicus. II. Characterization of Illuden S–Metabolizing Enzyme", *Xenobiotica, 22 (1)*, (1992),pp. 33–39.

Tanaka, K..,et al. , "Metabolism of Illuden S, a Toxic Principle of Lampteromyces Japonicus, by Rat Liver. I. Isolation and Identification of Cyclopropane Ring–Cleavage Metabolites", *Xenobiotica, 20 (7)*, (1990),pp. 671–681.

Varki, N..M. ,et al., "Cloned Low Metastic Variants from Human Lung Carcinoma Metastases", *Anticancer Research, 10*, (1990),pp. 637–644.

Vendetti, J..M. ,et al., "Current NCI Preclinical Antitumor Screening in Vivo: Results of Tumor Panel Screening, 1976–1982, and Future Directions", *Advances in Pharmacology and Chemotherapy, 20*, (1984),pp. 1–20.

Venditti, J..M. , "The National Cancer Institute Antitumor Drug Discovery Program, Current and Future Perspectives: A Commentary", *Cancer Treatment Reports, 67 (9)*, (Sep. 1983),pp. 767–772.

Walser, J..,et al. , "Mode of Action of Illuden S", *Antimicrobial Agents and Chemotherapy, 3 (3)*, (Mar. 1973),pp. 357–363.

Weinreb, S..M. , "Fulvenes Derived from Illuden S", *Tetrahedron Letters, 38*, (Sep. 1971),pp. 3489–3491.

*Primary Examiner*—Kathleen K. Fonda
*Assistant Examiner*—Leigh C. Maier
(74) *Attorney, Agent, or Firm*—Schwegman, Lundberg, Woessner & Kluth, P.A.

23  24  25

26  27  29

30  31  32

33  35

36

37

38

39

40

41

42

43

44　　　　　　　45　　　　　　　46

47　　　　　　　48　　　　　　　49

50

ILLUDIN ANALOGS USEFUL AS ANTITUMOR AGENTS

CROSS-REFERENCE TO RELATED APPLICATIONS

This application is a continuation of U.S. Patent Application No. 09/501,151 filed Feb. 9, 2000, issued on Apr. 30, 2002 as U.S. Pat. No. 6,380,403, which is a continuation of U.S. patent application Ser. No. 09/241,172, filed on Feb. 1, 1999, now U.S. Pat. No. 6,069,283, which is a division of U.S. patent application Ser. No. 08/683,687, filed on Jul. 18, 1996, now U.S. Pat. No. 5,932,553 which are incorporated herein by reference.

BACKGROUND OF THE INVENTION

A listing of human cancers for which chemotherapy has exerted a predominant role in increasing life span, approaching normal life expectancy, includes Burkitt's lymphoma, acute lymphocytic leukemia and Hodgkin's disease, along with about 10–15 other tumor types. For example, see A. Golden et al., *Eur. J. Cancer*, 17, 129 (1981) (Table 1). While the cure rate of these cancers illustrates the level of success of screening systems in selecting antitumor agents that are effective in man, these responsive tumors represent only a small fraction of the various types of cancer and, notably, there are relatively few drugs highly active against clinical solid tumors. Such drugs include cyclophosphamide, adriamycin, 5-FU, hexamethylmelamine and the like. Thus, patients with many types of malignancies remain at significant risk for relapse and mortality.

After relapse, some patients can be reinduced into remission with their initial treatment regimen. However, higher doses of the initial chemotherapeutic agent or the use of additional agents are frequently required, indicating the development of at least partial drug resistance. Recent evidence indicates drug resistance can develop simultaneously to several agents, including ones to which the patient was not exposed. The development of multiple-drug resistant (mdr) tumors may be a function of tumor mass and constitutes a major cause of treatment failure. To overcome this drug resistance, high-dose chemotherapy with or without radiation and allogenic or autologous bone marrow transplantation can be employed. The high-dose chemotherapy may employ the original drug(s) or be altered to include additional agents. The development of new drugs non-cross resistant with mdr phenotypes is required to further the curative potential of current regimens and to facilitate curative interventions in previously treated patients.

Recently, the in vitro anti-tumor activity of a novel class of natural products called illudins was examined by Kelner, M. et al., *Cancer Res.*, 47, 3186 (1987), incorporated herein by reference. Illudin M was purified and submitted for evaluation to the National Cancer Institute Division of Cancer Treatment (NCI DCT) in vivo drug screening program. Illudin M significantly increased the life span of rats with Dunning leukemia, but had a low therapeutic index in solid tumor systems. The extreme toxicity of illudins has prevented any applications in human tumor therapy. Recently, synthetic analogs of the illudins have been developed which exhibit promising antitumor activity, including U.S. Pat. Nos. 5,439,936 and 5,523490.

However, there exists a continuing need for chemotherapeutic agents which inhibit tumor growth, especially solid tumor growth, and which have an adequate therapeutic index to be effective for in vivo treatment.

SUMMARY OF THE INVENTION

The present invention provides illudin analogs of the general formula (I):

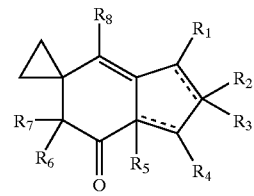

(I)

wherein $R_1$ is $(CH_2)_n$—(X)—(Y) or H; n is 0–4, X is O or S or N, and Y is $CH_2OC(O)$ $(C_1$–$C_4)$alkyl, $(C_1$–$C_8)$alkyl optionally substituted with 1–2 OH or 1–2 halo (Cl, Br, I or F); a saccharide, preferably a monosaccharide, preferably fructose; $CH_2C(O)$—O—$(CH_2)_2$—O—$C(O)CH_2SH$, $(CH_2)_2$—O—$(CH_2)_2W$ wherein W is halo; $(C_1$–$C_8)$alkyl—O—$(C_1$–$C_8)$alkyl; $(C_6$–$C_{10})$aryl, $(C_6$–$C_{10})$aryl$(C_1$–$C_4)$alkyl or $C(O)O(C_6$–$C_{10})$aryl, wherein the aryl moiety is optionally substituted with 1–2 OH, halo, $(C_1$–$C_4)$alkyl or $O(C_1$–$C_4)$alkyl; $CH_2CO_2(C_1$–$C_4)$alkyl, $CH_2CO_2H$, $Si((C_1$–$C_4)$alkyl)$_3$, an amino acid residue, preferably alanyl; or H with the proviso that when Y is H, n is 2–4; or X is absent, and Y is CHO, $NO_2$, COOH, OAc, $(C_2$–$C_4)$alkenyl-CHO, $CH(O(C_1$–$C_4)$alkyl)$_2$; cyclo$(C_3$–$C_6)$alkyl or $(C_5$–$C_{12})$aryl optionally comprising 1–3 heteroatoms selected from N, S, or non-peroxide O, optionally substituted with 1–2 $(C_1$–$C_4)$alkyl, CHO, OH or halo;

$R_2$ is absent; or $R_1$—C—C—$R_2$ together comprise a 5–7 membered ring, optionally comprising one or more, preferably 1–2, heteroatoms selected from N, S, or non-peroxide O, and optionally substituted with $(C_1$–$C_4)$alkyl, OH or halo;

$R_3$ is H or $(C_1$–$C_4)$alkyl;

$R_4$ is H, $SCH_2CO_2(C_1$–$C_4)$alkyl, O—$(C_5$–$C_{12})$aryl or S—$(C_5$–$C_{12})$aryl where aryl is optionally substituted with halo, OH or $(C_1$–$C_4)$alkyl;

$R_5$ is H, OH or absent;

$R_6$ is $(C_1$–$C_4)$alkyl or H; and $R_7$ is OH or $Si((C_1$–$C_4)$alkyl)$_3$; or $R_6$ and $R_7$ together are ethylenedioxy;

$R_8$ is $(C_1$–$C_4)$alkyl, optionally substituted with OH or halo;

the bonds represented by—are present or absent; and the pharmaceutically acceptable salts thereof.

Preferably when X is absent, n is 2 to 4.

The present invention also provides compounds of formula (I) wherein the cyclopropyl group is replaced with —$(CH_2)_2OH$, and the carbonyl oxygen is replaced with a hydroxyl group, yielding compounds of the formula (II)

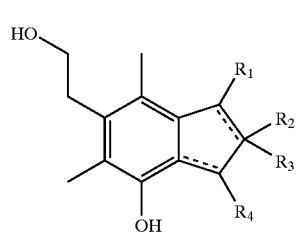

(II)

where $R_1$–$R_4$ are defined as in Formula (I), and the bonds represented by—are individually present or absent. Preferably, however, $R_1$ is $(C_1$–$C_4)$alkyl-Z where Z is OH or halo, or —S—$(C_5$–$C_{12})$aryl, preferably —S-phenyl, and the aryl group is optionally substituted with 1–2 OH, halo or $(C_1$–$C_4)$alkyl; $R_2$ is absent; $R_3$ is $(C_1$–$C_4)$alkyl, preferably Me; and $R_4$ is —S—$(CH_2)_n$—COOH where n is 1–4 or $R_4$ is —S-aryl, preferably —S-phenyl, and the aryl group is optionally substituted with 1–2 OH, -halo or $(C_1$–$C_4)$alkyl.

The invention also provides dimeric compounds comprising compounds of formula (I), wherein the monomeric illudin analogs are the same or different. For example, in formula (I) $R_1$ and $R_4$ can be a compound of formula (I) wherein X and Y are absent. Thus, the invention also provides dimeric compounds comprising compounds of formula (I) wherein the structure of the monomeric compounds is the same or different. Typically, the dimers are of the formula (III)

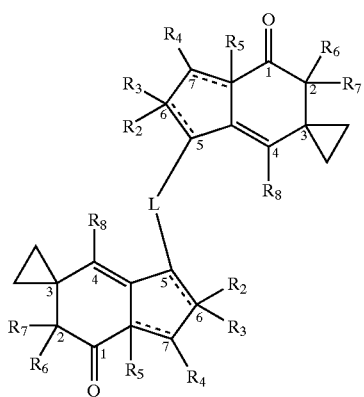

(III)

where L is a linker group. L may be, by way of example, an alkyl or ester based linker group. Examples of suitable linker groups include —$CH_2$—O—$CH_2$—, —$(CH_2)_n$— where n is 1 to 8, and —$CH_2$—S—$CH_2C(O)$—O—$(CH_2)_2$—O—$C(O)$ $CH_2$—S—$CH_2$—. Other linker groups would be apparent to one skilled in the art. Although shown linked via the 5-position carbons of each analog, it is understood that the analogs may be linked via other positions, such as any combination of the 3-, 5- or 7-position carbon atoms. Where linkage is via a position other than the 5-position, the substituent $R_1$ will be present, and as defined for Formula (I). Where linkage is via the 3-position, it is understood that the cyclopropyl moiety will not be present. Where linkage is via the 5-position carbon of each analog, L is preferably —$CH_2$—O—$CH_2$— or —$CH_2$—S—$CH_2C(O)$—O—$(CH_2)_2$—O—$C(O)CH_2$—S—$CH_2$—.

These compounds are useful as antineoplastic agents, i.e., to inhibit tumor cell growth in vitro or in vivo, in mammalian hosts, such as humans or domestic animals, and are particularly effective against solid tumors and multi-drug resistant tumors.

Thus, the present invention provides a therapeutic method to treat cancer, i.e., to inhibit tumor cell growth in vitro, or preferably, in AYE, by administration to a mammal, such as a human cancer patient, of an amount of a compound of formula I effective to inhibit the growth of said cancer cells, i.e., tumor cells. The present compounds may be particularly useful for the treatment of solid tumors for which relatively few treatments are available. Such tumors include epidermoid and myeloid tumors, acute (AML) or chronic (CML), as well as lung, ovarian, breast and colon carcinoma. The present compounds can also be used against endometrial tumors, bladder cancer, pancreatic cancer, lymphoma, Hodgkin's disease, prostate cancer, sarcomas and testicular cancer as well as against tumors of the central nervous system, such as brain tumors, neuroblastomas and hematopoietic cell cancers such as B-cell leukemia/lymphomas, myelomas, T-cell leukemiallymphomas, and small cell leukemia/lymphomas. These leukemia/lymphomas could be either acute (ALL) or chronic (CLL).

The present compounds may also be targeted to a particular tumor by attaching the compound to a reagent which is capable of binding to a tumor-associated antigen. The antigen may be located on a tumor or in the tumor cell area. Suitable reagents include polyclonal and monoclonal antibodies. The compound-reagent complex may further comprise a linker for attaching the compound to the reagent.

The present invention also provides pharmaceutical compositions, such as pharmaceutical unit dosage forms, comprising an effective anti-neoplastic amount of one or more of the present illudin analogs in combination with a pharmaceutically acceptable carrier.

As used herein, with respect to the present method, the term "inhibit" means either decreasing the tumor cell growth rate from the rate which would occur without treatment, or causing the tumor cell mass to decrease in size. Inhibiting also includes causing a complete regression of the tumor. Thus, the present analogs can either be cytostatic or cytotoxic to the tumor cells.

The subject can be any mammal having a susceptible cancer, i.e., a malignant cell population or tumor. The analogs are effective on human tumors in v as well as on human tumor cell lines in vitro.

DETAILED DESCRIPTION OF THE INVENTION

Figure 1A:
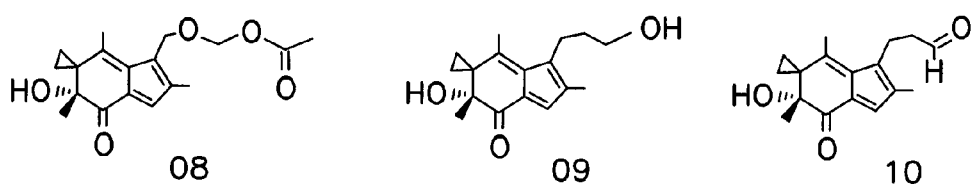
FIGS. 1A–1E are schematics of representative compounds of the invention.
Figure 1A:
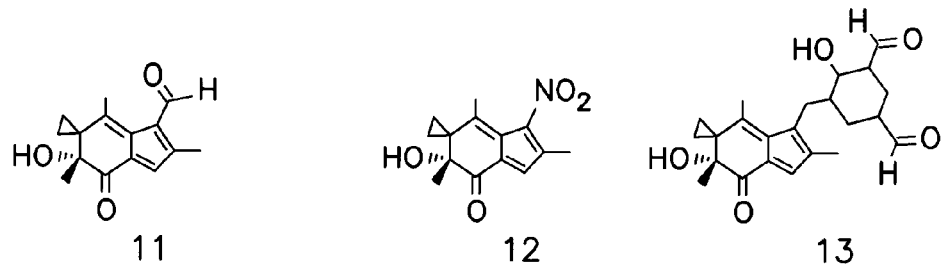
Figure 1A:
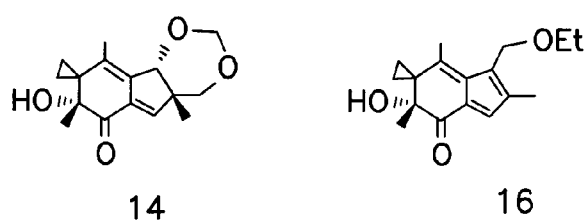
Figure 1A:
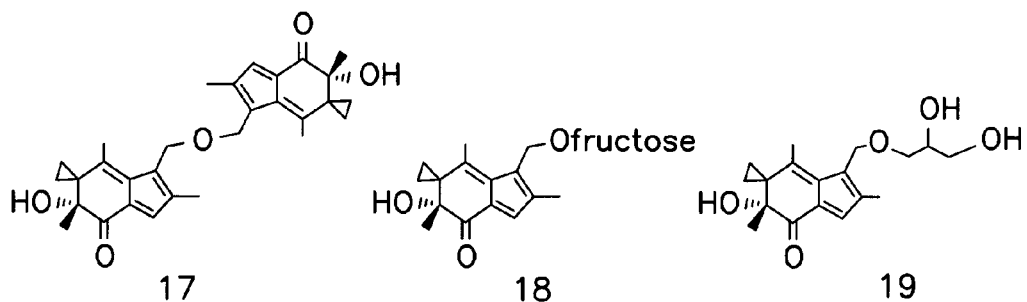
Figure 1A:
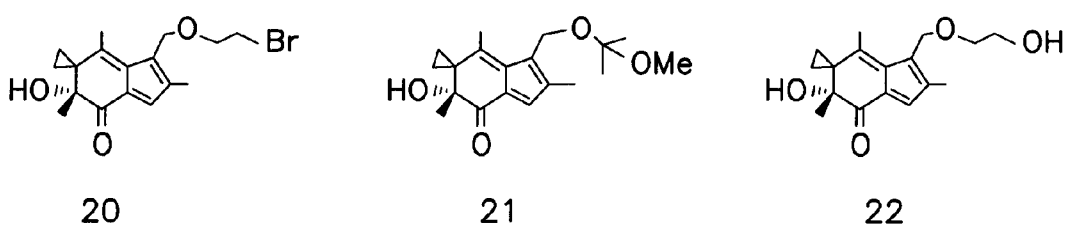
Figure 1B:
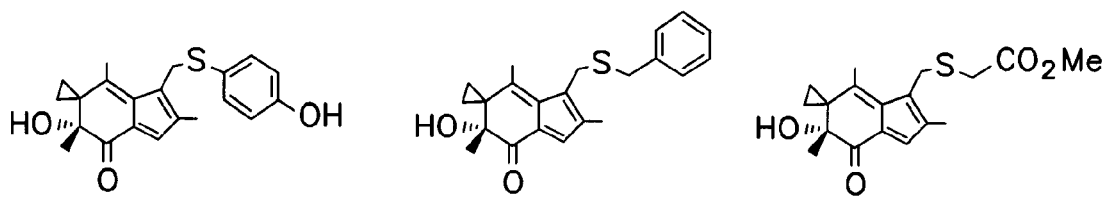
Figure 1B:
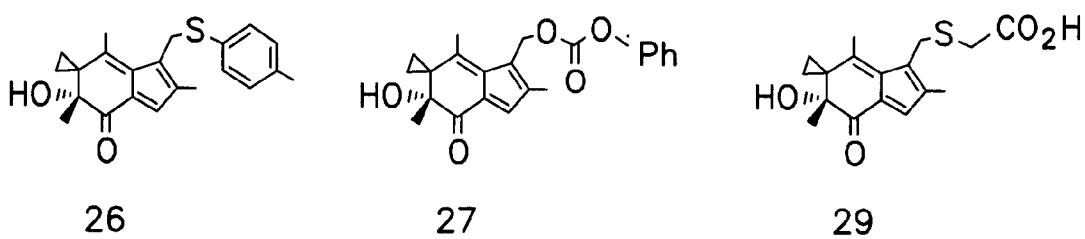
Figure 1B:
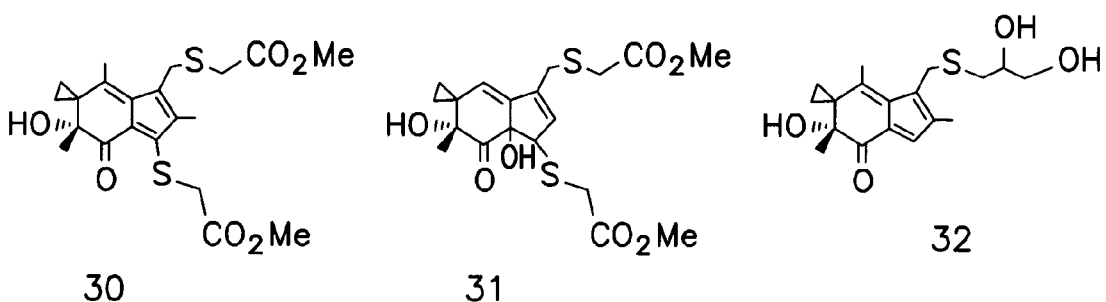
Figure 1B:
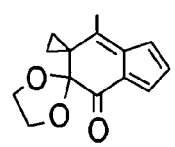
Figure 1B:
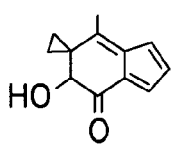
Figure 1C:
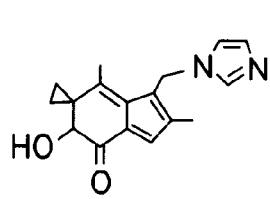
Figure 1C:
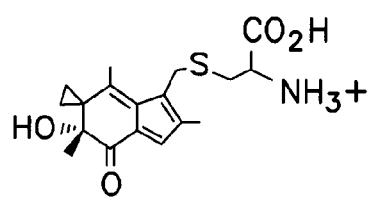
Figure 1C:
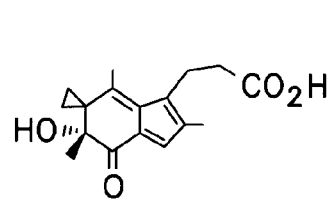
Figure 1C:
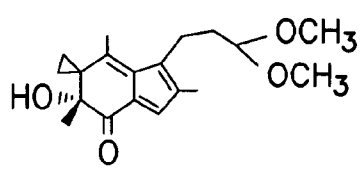
Figure 1C:
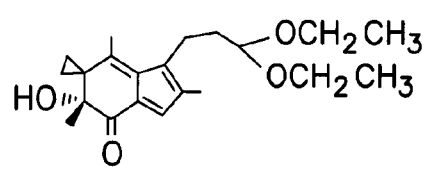
Figure 1C:
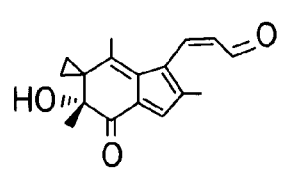
Figure 1C:
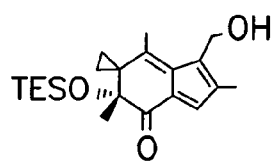
Figure 1C:
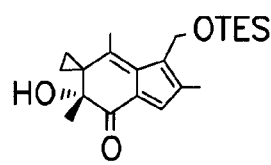
Figure 1D:
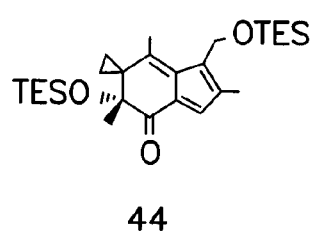
Figure 1D:
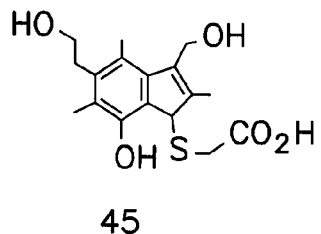
Figure 1D:
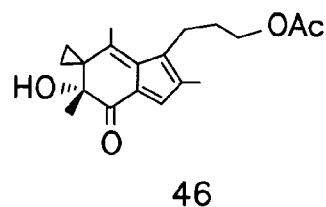
Figure 1D:
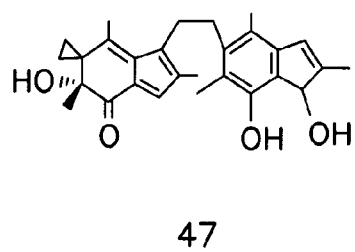
Figure 1D:
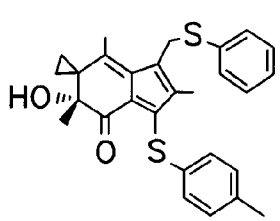
Figure 1D:
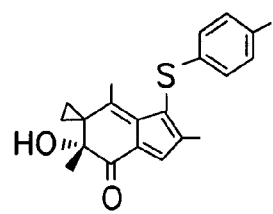
Figure 1D:
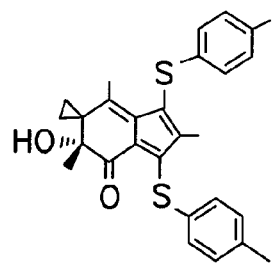
Figure 1E:
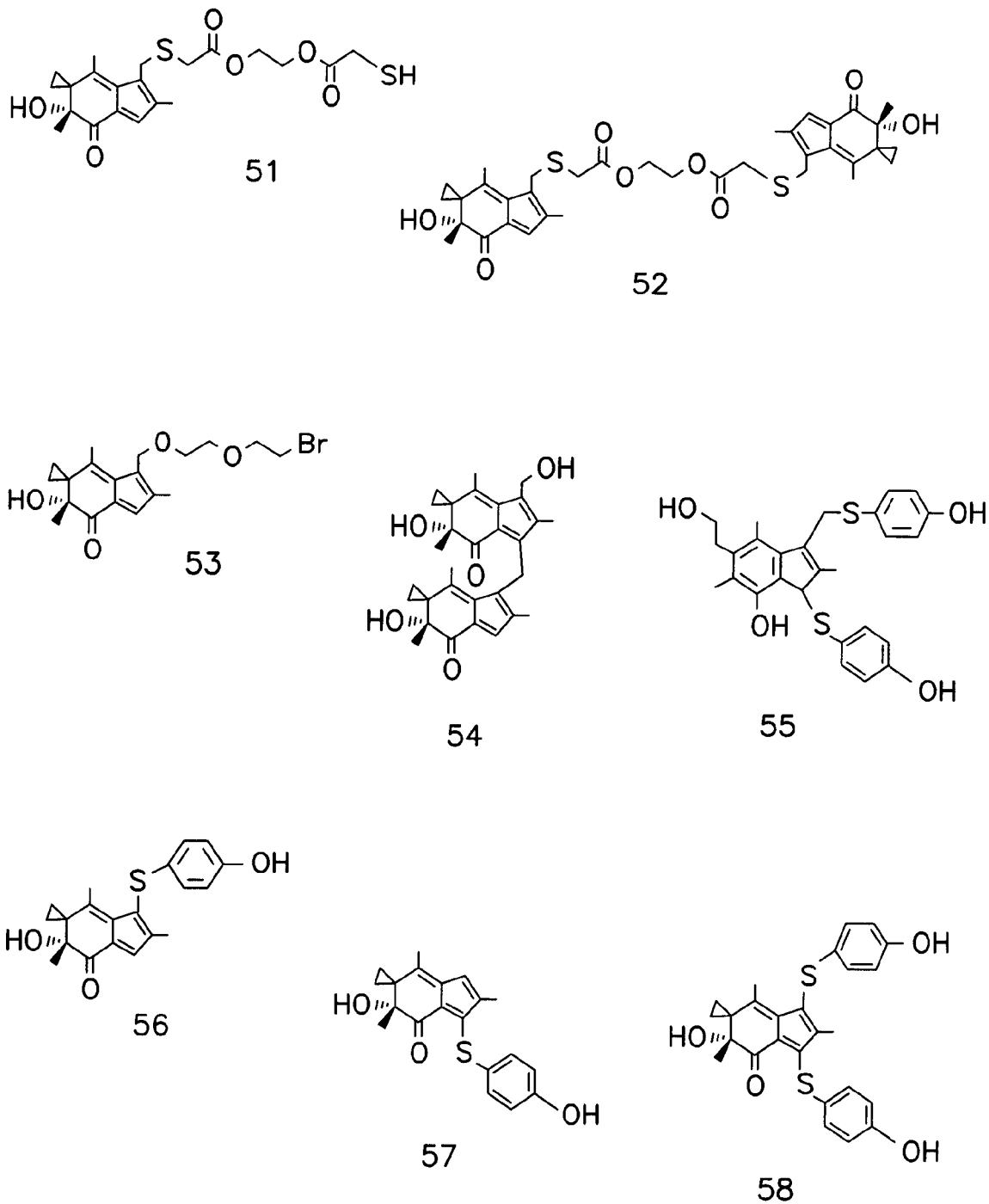

The present invention provides illudin analogs of the general formula (I):

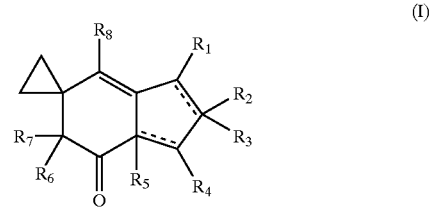

(I)

wherein $R_1$ is $(CH_2)_n$—(X)—(Y) or H; n is 0–4, preferably n is 2–4 when X is absent; X is O or S or N; and Y is $CH_2OC(O)(C_1$–$C_4)$alkyl, $(C_1$–$C_8)$alkyl optionally substituted with 1–2 OH or 1–2 halo, a saccharide, preferably a monosaccharide, preferably fructose, $CH_2C(O)$—O—$(C_2)_2$—O—$C(O)CH_2SH$, $(CH_2)_2$—O—$(CH_2)_2W$ where W is halo; $(C_1$–$C_8)$alkyl—O—$(C_1$–$C_8)$alkyl, preferably $(C_1$–$C_4)$ alkyl—O—$(C_1$–$C_4)$alkyl; $(C_6$–$C_{10})$aryl, $(C_6$–$C_{10})$aryl $(C_1$–$C_4)$alkyl or $C(O)O(C_6$–$C_{10})$aryl wherein the aryl moiety is optionally substituted with 1–2 OH, halo, $(C_1$–$C_4)$ alkyl or $O(C_1$–$C_4)$alkyl; $CH_2CO_2(C_1$–$C_4)$alkyl, $CH_2CO_2H$, $Si((C_1$–$C_4)$alkyl)$_3$, an amino acid residue, preferably alanyl; or H with the proviso that when Y is H, n is 2–4; or X is absent, and Y is CHO, $NO_2$, $NH_2$, OH, COOH, OAc, $(C_2$–$C_4)$alkenyl-CHO, $CH(O(C_1$–$C_4)$alkyl)$_2$; cyclo($C_3$–$C_6$)

alkyl or $(C_5-C_{12})$aryl, preferably $C_5$ aryl, optionally comprising 1–3 heteroatoms selected from N, S, or non-peroxide O, optionally substituted with 1–2 $(C_1-C_4)$alkyl, CHO, OH or halo;

$R_2$ is absent; or $R_1$—C—C—$R_2$ together comprise a 5–7 membered cyclic ring, said ring optionally comprising one or more heteroatoms selected from N, S, or non-peroxide O, and optionally substituted with $(C_1-C_4)$alkyl, OH or halo;

$R_3$ is H or $(C_1-C_4)$alkyl;

$R_4$ is H, $SCH_2CO_2(C_1-C_4)$alkyl, O—$(C_5-C_{12})$aryl or S—$(C_5-C_{12})$aryl where aryl is optionally substituted with halo, OH or $(C_1-C_4)$alkyl;

$R_5$ is H, OH or absent;

$R_6$ is $(C_1-C_4)$alkyl or H;

$R_7$ is OH or $(Si((C_1-C_4)alkyl)_3)$; or $R_6$ and $R_7$ together are ethylenedioxy;

$R_8$ is $(C_1-C_4)$alkyl optionally comprising OH or halo; and the bonds represented by—are individually present or absent.

In a further preferred embodiment, X is absent, n is 2 to 4, and Y is OH or OAc.

In a particularly preferred embodiment, $R_1$ is $(CH_2)_n$—X—Y where n is 1, X is O or S and Y is $(C_1-C_8)$alkyl optionally substituted with 1–2 OH or 1–2 halo, or —$C(CH_3)_2O(C_1-C_4)$alkyl; where preferably $R_2$ and $R_5$ are absent; $R_3$, $R_6$ and $R_8$ are $CH_3$; $R_4$ is H; and $R_7$ is OH.

According to another preferred embodiment of the invention, $R_6$ and $R_7$ together are ethylenedioxy, and $R_1$ is H; $R_2$ and $R_5$ are absent; $R_3$ and $R_4$ are H, and $R_8$ is $CH_3$.

In another embodiment, $R_1$ is $CH_2OH$ and $R_7$ is —$OSi((C_1-C_4)alkyl)_3$.

As used herein, the term "alkyl" includes branched or straight-chain alkyl groups.

As used herein, the term "saccharides" includes monosaccharides comprising up to 8 carbons, preferably up to 6 carbons, as well as disaccharides. The term includes glucose, fructose and ribose, as well as deoxy sugars such as deoxyribose and the like.

The compounds shown in FIG. 1 are representative of the present invention.

The compounds of the present invention may be derived from illudin S, 6-hydroxymethyl acylfulvene (HMAF, i.e., the compound of formula (I) wherein $R_1$ is $CH_2OH$, $R_2$ is absent, $R_3$ is $CH_3$, $R_4$ is H, $R_5$ is absent, $R_6$ is $CH_3$, $R_7$ is OH and $R_8$ is $CH_3$) and fulvene (i.e., a compound of formula (I) wherein $R_1$ is H, $R_2$ is absent, $R_3$ is $CH_3$, $R_4$ is H, $R_5$ is absent, $R_6$ is $CH_3$, $R_7$ is OH and $R_8$ is $CH_3$) the syntheses of which are known in the art (see e.g., WO 91/04754; WO 94/18151).

The following compounds of formula (I) where X is S or O, may be prepared by adding the appropriate reagent to an acidic solution of HMAF, unless otherwise noted.

Where Y is $(C_1-C_8)$alkyl, an alkyl ether is used. For example, compound 16 (where Y is ethyl) was prepared using ethyl ether. Where Y is $(C_1-C_8)$alkyl substituted with 1–2 OH or 1–2 halogen, the appropriate alcohol or thiol, halogenated where required, was added. For example, for compounds 19, 20 and 22 where X is O and Y is 2,3 dihydroxypropyl, 2-bromo ethyl and 2-hydroxyethyl; glycerol, 2-bromoethanol and ethylene glycol, respectively, were used. Compounds wherein Y is $CH_2OC(O)(C_1-C_4)$alkyl, are prepared by reacting compounds wherein $R_1$ is $(CH_2)_nOCH_2OH$ with $(C_1-C_4)$alkyl$C(O)$Cl in the presence of base. Compound 53 was formed as a by product in the synthesis of compound 20. For compound 32, where X is S and Y is 2,3 dihydroxypropyl, thioglycerol was employed as the reagent.

The appropriate saccharide is used to synthesize compounds of formula (1) where Y is a monosaccharide. For example, compound 18 was made using fructose.

Where Y is $CH_2C(O)$—$O(CH_2)_2$—O—$C(O)CH_2SH$, i.e., compound 51, a controlled amount of glycol dimercaptoacetate is employed as the reagent.

Where Y is $(CH_2)_2$—(O)—$(CH_2)_2W$ where W is halo, the appropriate halogenated alcohol is used. For example, compound 53 was obtained by adding 2-bromoethanol.

Compounds of formula (1) where Y is $(C_1-C_8)$alkyl—O—$(C_1-C_8)$alkyl, where $(C_1-C_8)$alkyl is straight chain alkyl, may be prepared using a method analogous to that used to prepare compound 53. Where $(C_1-C_8)$alkyl is branched, the desired product may be obtained by the addition of an appropriate alkene to HMAF along with a catalytic amount of $POCl_3$. For example, compound 21, where Y is 2-methoxy-2-prop-yl, was prepared by adding 2-methoxypropene to HMAF.

Where Y is $(C_6-C_{10})$aryl or $(C_6-C_{10})$aryl$(C_1-C_4)$alkyl, compounds may be prepared using a thioaryl or aryl mercaptan as the reagent. For example, compound 23, where Y is $(C_6H_4)$OH, was prepared by adding 4-hydroxythiophenol. Compound 55 was obtained as a by product in the synthesis of compound 23. Compound 24 was prepared by adding benzyl mercaptan to an acidic solution of HMAF. Compound 26, where X is S and Y is 4-methylbenzene, was prepared by adding p-thiocresol to an acidic solution of HMAF. Compound 48, where Y is 4-methylbenzene and $R_4$ is thiocresol, was obtained as a by product when limited p-thiocresol was used to prepare compound 26. Compounds 49 and 50, where n=0, X is S, Y is 4-methylbenzene and $R_4$ is H or thiocresol, respectively, were prepared by adding p-thiocresol to an acidic solution of acylfulvene. Compounds where Y is $C(O)O(C_6-C_{10})$aryl may be prepared by adding the appropriate aryl chloroformate to a basic solution of HMAF. For example, compound 27, where Y is phenylacetate, was prepared by adding phenyl chloroformate and pyridine to a solution of HMAF.

Compounds where Y is $CH_2CO_2(C_1-C_4)$alkyl and X is S may be prepared by adding the appropriate thiol to an acidic solution of HMAF. For example, compound 25 where Y is $CH_2CO_2Me$ and $R_4$ and $R_5$ are H, was prepared by adding methylthioglycolate to an acidic solution of HMAF in acetone. Compounds 30 and 31 where Y is $CH_2CO_2Me$, $R_4$ is $CH_2CO_2Me$ and $R_5$ is H and OH, respectively, were prepared by adding methylthioglycolate to a neutral solution of HMAF in acetone and THF. Compound 45 was formed as a by product.

Compounds where Y is $CH_2CO_2H$ may be prepared via hydrolysis of the corresponding esters. For example, compound 29 was prepared as a by product in the synthesis of compound 25 described above. Alkali metal, alkaline earth metal and amine salts of the $CO_2H$ group are also within the scope of the invention.

Where Y is $Si((C_1-C_4)alkyl)_3$, the appropriate silanating reagent is added to a solution of HMAF and imidazole. For example, compounds 43 and 44 where $R_1$ is triethylsiloxy and $R_7$ is OH or triethylsiloxy, respectively, were both obtained when triethylsilylchloride was added to a solution of HMAF and imidazole in DMF.

Where Y is an amino acid residue, for example, glycyl or alanyl, the appropriate thiol containing amino acid analog may be used, such as cysteine and analogs thereof. For example, compound 37, where Y is glycyl, was prepared by adding cysteine to an acidic solution of HMAF.

Compounds of formula (I) where X is absent may be prepared as follows. Compounds where n is 2 and Y is CHO, i.e., compound 10, may be obtained by adding acrolein to an acidic solution of fulvene. Compound 11, where n is 1 and Y is CHO, was prepared via oxidation of HMAF with Dess Martin reagent.

Compounds where Y is $CH(O(C_1-C_4)alkyl)_2$ may be obtained by reduction of compound 10 in appropriate solvent. For example, compound 39 where Y is $CH(OMe)_2$ was obtained by reacting compound 10 with sodium borohydride in methanol. Compound 40 where Y is $CH(OEt)_2$ was prepared by reacting compound 10 with sodium borohydride in ethanol.

Compounds where Y is —$(C_2-C_4)$alkenyl-CHO may be obtained by adding the appropriate alkynyl aldehyde to an acidic solution of HMAF. For example, compound 41 where Y is —CH=CHCH(O) was obtained by treating an acidic solution of HMAF with propargyl aldehyde.

Compounds where Y is cyclo($C_3-C_6$)alkyl may be prepared by methods known in the art. For example, compound 13 was prepared in the synthesis of compound 10.

Where Y is ($C_5-C_{12}$)aryl, or heteroaryl, the appropriately substituted aryl or heteroaryl reagent is added to acidic, basic or neutral HMAF. For example, compound 36 where Y is an imidazole group, as prepared by treating a neutral solution of HMAF in THF with imidazole.

Compounds where X is absent and n is 2–4 may be prepared as follows. Compounds where Y is OH may be obtained via reduction of the corresponding aldehyde or acid with an appropriate reducing agent. For example, compound 9 was obtained via reduction of the aldehyde compound 10 with sodium cyanoborohydride and acetic acid. The presence of acetic acid can yield compounds where Y is OAc. For example, compound 46 was obtained as a by product of the reduction reaction of compound 10.

Compounds where $R_1$—C—C—$R_2$ comprises a 5–7 membered ring may be prepared by methods known in the art. By way of example, compound 14 was prepared by adding illudin S to an acidic solution of paraformaldehyde.

Compounds where $R_1$ is $CH_2OH$ and $R_7$ is (($C_1-C_8$)alkyl)$_3$SiO— may be obtained by treating HMAF and imidazole with an appropriate silanating reagent. For example, compound 42 was prepared by adding triethylsilyl chloride to HMAF and imidazole.

Compound 38 where Y is COOH was prepared by oxidizing compound 10 with Jones Reagent.

Dimeric compounds of formula (III) may be prepared by methods known in the art. For example, compound 17 was prepared by adding ethyl ether to an acidic solution of HMAF and acetone. Compound 47 was obtained as a by product when acrylonitrile was added to an acidic solution of HMAF and acetone. Compound 54 was obtained as a by product in the synthesis of HMAF. Compound 52 was obtained during the synthesis of compound 51.

Pharmaceutically acceptable salts include, where applicable, salts such as amine acid addition salts and the mono-, di- and triphosphates of free hydroxyl groups. Amine salts include salts of inorganic and organic acids, including hydrochlorides, sulfates, phosphates, citrates, tartarates, malates, maleates, bicarbonates, and the like. Alkali metal amine or ammonium salts can be formed by reacting hydroxyaryl groups with metal hydroxides, amines or ammonium.

The compounds of the present invention can be formulated as pharmaceutical compositions and administered to a mammalian host, such as a human cancer patient, in a variety of forms adapted to the chosen route of administration, i.e., orally or parenterally, by intravenous, intraperitoneal, intramuscular or subcutaneous routes.

Thus, the present compounds may be orally administered, for example, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between 2 to about 60% of the weight of a given unit dosage form. The amount of active compound in such therapeutically useful compositions is such that an effective dosage level will be obtained.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose, or saccharin or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion use can include sterile aqueous solutions or dispersions or sterile powders comprising the active ingredient which are adapted for the extemporaneous preparation of sterile injectable of infusible solutions or dispersions. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersion or by the use of surfactants. The prevention of the action of microorganisms can be brought about by various antibacterial and antifungal agents, or example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin. Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the compounds of FIGS. 1A–1E can be determined by correlating their in vitro activity, and in vivo activity in animal models, such as murine or dog models as taught for illudin analogs such as those of U.S. Pat. Nos. 5,439,936 and 5,523,490, to activity in higher mammals, such as children and adult humans as taught, e.g., in Borch et al. (U.S. Pat. No. 4,938,949).

The therapeutically effective amount of analog necessarily varies with the subject and the tumor to be treated. However, it has been found that relatively high doses of the analogs can be administered due to the decreased toxicity compared to illudin S and M. A therapeutic amount between 30 to 112,000 µg per kg of body weight is especially effective for intravenous administration while 300 to 112,000 µg per kg of body weight is effective if administered intraperitoneally. As one skilled in the art would recognize, the amount can be varied depending on the method of administration.

The invention will be further described by reference to the following detailed examples.

EXAMPLES

Example I

Synthesis of Illudin Analogs

General. Melting points are uncorrected. $^1$H and $^{13}$C NMR spectra were measured at 300 and 75 MHz. High resolution mass spectra were determined at the University of Minnesota Mass Spectrometry Service Laboratory. All chromatography used silica gel (Davisil 230–425 mesh, Fisher Scientific) and solvent was ethyl acetate and hexanes except being mentioned specifically. Analytical TLC was carried out on Whatman 4420 222 silica gel plates. Reactions were routinely monitored by TLC.

Synthesis of illudin S, hydroxymethylacylfulvene (HMAF) and fulvene are known in the art (see, e.g., WO 91/04754; WO 94/18151).

Compound 11. To a stirred solution 103.5 mg HMAF (MW 246, 0.406 mmol) in 15 ml $CH_2Cl_2$ was added 327 mg Dess-Martin reagent. The mixture was stirred at room temperature for 1 h and was partitioned between ethyl ether and saturated $NaHSO_4$ and $NaHCO_3$ solution (1:1). The organic extracts were washed with saline until neutral. After being dried by $MgSO_4$, the solution was concentrated and chromatographed to give 65.7 mg 11 (64.0%). 11 is a yellow gum: $^1$H NMR ($CDCl_3$) δ0.83 (m, 1H), 1.19 (m, 1H), 1.41 (s, 3H), 1.45 (m, 1H), 1.67 (m, 1H) 2.31 (s, 3H), 2.50 (s, 3H), 3.80 (s, 1H), 7.08 (s, 1H), 10.25 (s, 1H); MS m/z 244M$^+$); UV λmax 241 nm (ε14000), 293 nm (ε12000).

Compound 12. (6-Nitroacylfulvene). Acylfulvene (99 mg, 0.46 mmol) was dissolved in methylene chloride (20 mL) and nitronium tetrafluoroborate (141 mg, 1.1 mmol) was added to the solution (nitrogen atmosphere). A dark brown precipitate formed; the mixture was stirred for 4 h, more nitronium tetrafluoroborate was added (53 mg) and stirring continued for 2 h. Water (5 mL) was added and the mixture was extracted with methylene chloride (3×25 mL). The combined extracts were washed with saturated $NaHCO_3$ solution, water, then dried over $MgSO_4$. Removal of solvent and chromatography of the residue with hexane-ethyl acetate gave the nitro compound 12 as a yellow solid (30 mg); $^1$H NMR δ0.90 (ddd, 1H), 1.23 (ddd, 1H), 1.50 (ddd, 1H), 1.69 (ddd, 1H), 1.46 (s, 3H), 2.02 (s, 3H), 2.34 (s, 3H), 6.97 (s, 1H), MS m/z 261 (M$^+$ —CH$_3$), 244 (M$^+$—OH), 215 (M$^+$—NO$_2$).

Compound 14. To a solution of 250 ml of 1M $H_2SO_4$ and 200 ml acetone was added 40 g paraformaldehyde (MW 30, 1.33 mol). The solution was heated to clear and was then allowed to cool to room temperature. 1 g illudin S (MW 264, 3.79 mmol) was added to the above solution. The mixture was stirred at room temperature for 72 h and was partitioned between ethyl acetate and water. The organic extracts were washed by saturated $NaHCO_3$ and saline respectively to neutral. After being dried by $MgSO_4$, the solution was concentrated and chromatographed to give 245 mg 14 (23.4%) and 226 mg HMAF (24.3%). 14 is a white crystal: mp 100.5–102.5; IR (KBr) 3469, 2966, 2858, 1703, 1656, 1596, 1172 cm$^{-1}$; $^1$H NMR ($CDCl_3$) δ0.48 (m, 1H), 0.84 (m, 1H), 0.99 (m, 1H), 1.10 (s, 3H), 1.17 (m, 1H), 1.32 (s, 3H), 1.67 (s, 3H), 3.61 (s, 1H), 3.73 (d, J=11.7 Hz, 1H), 3.96 (d, J=11.7 Hz, 1H), 4.56 (s, 1H), 4.75 (d, J=5.4 Hz, 1H), 4.91 (d, J=5.4 Hz, 1H), 6.52 (s, 1H); $^{13}$C NMR ($CDCl_3$) δ199.7, 141.4, 136.5, 135.9, 134.7, 90.0, 80.3 75.9, 70.8, 46.8, 32.3, 24.7, 22.5, 13.8, 8.9, 5.6; MS m/z 276 (M$^+$), 217, 201, 173; HRMS for $C_{16}H_{20}O_4$ calcd 276.1362, found 276.1364; UV λ$_{max}$ 305 nm (ε3148).

Compound 23. To the solution of 170 mg HMAF (MW 246, 0.691 mmol) in 15 ml acetone and 1 M $H_2SO_4$ solution (1:1) was added 63 mg 4-hydroxyl thiophenol (MW 126, 0.5 mmol). The mixture was stirred at room temperature for two hours and was partitioned between ethyl acetate and water. The organic extracts were washed by saturated $NaHCO_3$ and saline respectively to neutral. After being dried by $MgSO_4$, the solution was concentrated and chromatographed to give 128 mg 23 (72.3%) as yellow gum: IR (KBr) 3360, 2974, 1646, 1592, 1588, 1495 cm$^{-1}$; $^1$H NMR ($CDCl_3$) δ0.75 (m, 1H), 1.09 (m, 1H), 1.38 (m, 1H), 1.42 (s,3H), 1.52 (m, 1H), 1.70 (s, 3H), 2.14 (s, 1H), 3.96 (q, J$_{AB}$=13.2 Hz, 2H), 6.77 (d, J=8.4 Hz, 2H), 7.07 (s, 1H), 7.20 (d, J=8.4 Hz, 1H); $^{13}$C NMR ($CDCl_3$) δ197.9, 159.6, 156.7, 142.4, 138.2, 136.0, 135.9, 132.9, 131.5, 125.8, 123.6, 116.1, 115.9, 76.2, 37.6, 34.2, 27.8, 16.3, 14.2, 12.5, 9.5; MS m/z 354 (M$^+$), 298, 270, 229; HRMS for $C_{21}H_{22}O_3S$ calcd 354.1296, found 354.1286; UV λmax (methanol) 332 nm (ε7844).

Compound 24. To the solution of 117 mg HMAF (MW 246,0.475 mmol) in 15 ml acetone and 1 M $H_2SO_4$ solution (1:1) was added 46 mg benzyl mercaptan (MW 124, 0.371 mmol). The mixture was stirred at room temperature for overnight and was partitioned between ethyl acetate and water. The organic extracts were washed by saturated $NaHCO_3$ and saline respectively to neutral. After being dried by $MgSO_4$, the solution was concentrated and chromatographed to give 100 mg 24 (76.6%) as yellow gum: IR (KBr) 3451, 2980, 1659, 1598, 1496, 1097 cm$^{-1}$, $^1$H NMR ($CDCl_3$) δ0.64 (m, 1H), 1.02 (m, 1H), 1.29 (m, 1H), 1.33 (s, 3H), 1.46 (m, 1H), 1.91 (s, 3H), 1.98 (s, 3H), 3.62 (s, 2H), 3.71 (s, 2H), 7.06 (s, 1H), 7.29 (m, 5H); $^{13}$C NMR ($CDCl_3$) δ197.2, 159.5, 141.8, 138.4, 137.8, 134.9, 130.1, 128.7, 128.3, 126.9, 126.0, 75.9, 37.5, 36.8, 28.6, 27.5, 15.7, 14.1, 12.8, 9.3; MS m/z 352 (M$^+$), 294, 229; HRMS for $C_{22}H_{24}O_2S$ calcd 352.1497, found 352.1488; UV λmax (methanol) 332 nm (ε8431).

Compound 25 & 29. To the solution of 166 mg HMAF (MW 246, 0.675 mmol) in 15 ml acetone and 1 M $H_2SO_4$ solution (1:1) was added 51 mg methyl thioglycolate (MW 106, 0.481 mmol). The mixture was stirred at room temperature for overnight and was partitioned between ethyl acetate and water. The organic extracts were washed by saturated $NaHCO_3$ and saline respectively to neutral. After being dried by $MgSO_4$, the solution was concentrated and chromatographed to give 59 mg 25 (36.7%) and 94 mg 29 (61.1%). 25 is a yellow gum: IR (KBr) 3451, 2944, 1731, 1665, 1592, 1496, 1278 cm$^{-1}$; $^1$H NMR (CDCl$_3$) δ 0.72 (m, 1H), 1.07 (m, 1H), 1.35 (m, 1H), 1.37 (s, 3H), 1.49 (m, 1H), 2.12 (s, 3H), 2.16 (s, 3H), 3.23 (s, 2H), 3.74 (s, 3H), 3.92 (q, $J_{AB}$=12.3 Hz, 2H), 7.09 (s, 1H); $^{13}$C NMR (CDCl$_3$) δ197.5, 170.7, 159.6, 142.5, 138.3, 134.7, 129.1, 126.5, 76.1, 52.3, 37.6, 33.2, 29.6, 27.5, 16.1, 14.2, 12.9, 9.5; UV λmax (methanol) 334 nm (ε8093). 29 is also a yellow gum: $^1$H NMR (CDCl$_3$) δ0.73 (m, 1H), 1.09 (m, 1H), 1.32 (m, 1H), 1.37 (s, 3H), 1.50 (m, 1H), 2.12 (s, 3H), 2.16 3.25 (s, 2H), 3.93 (m, 2H), 7.11 (s, 1H); $^{13}$C NMR (CDCl$_3$) δ197.8, 174.7, 159.8, 142.7, 138.2, 135.1, 129.4, 126.4, 76.1, 37.7, 33.2, 29.6, 27.6, 16.2, 14.3, 12.9, 9.5

Compound 26. To the solution of 125 mg HMAF (MW 246, 0.508 mmol) in 20 ml acetone and 1 M $H_2SO_4$ solution (1:1) was added 59 mg p-thiocresol (MW 124, 0.476 mmol). The mixture was stirred at room temperature for 5 h and was partitioned between ethyl acetate and water. The organic extracts were washed by saturated $NaHCO_3$ and saline respectively to neutral. After being dried by $MgSO_4$, the solution was concentrated and chromatographed to give 127 mg 26 (75.8%) as yellow gum: IR (KBr) 3456, 2972, 1663, 1596, 1500, 1092 cm$^{-1}$; $^1$H NMR (CDCl$_3$) δ0.71 (m, 1H), 1.07 (m, 1H), 1.32 (m, 1H), 1.38 (s, 3H), 1.50 (m, 1H), 1.82 (s, 3H), 2.14 (s, 3H), 2.31 (s, 3H), 3.97 (s, 1H), 4.04 (q, JAB=12.9 Hz, 2H), 7.05 (s, 1H), 7.07 (d, q=8.1 Hz, 2H), 7.23 (d, q=7.8 Hz, 2H); $^{13}$C NMR (CDCl$_3$) δ197.3, 159.2, 142.3, 138.4, 137.3, 135.0, 132.2, 131.3, 129.8, 129.5, 126.1, 76.0, 37.5, 33.1, 27.6, 21.0, 16.1, 14.1, 12.6, 9.4; MS m/z 352 (M$^+$), 297, 250, 229; HRMS for $C_{22}H_{24}O_2S$ calcd 352.1497, found 352.1499; UV λmax (methanol) 333 nm (ε6598).

Compound 32. To the solution of 195 mg HMAF (MW 246, 0.793 mmol) in 10 ml acetone and 1 M $H_2SO_4$ solution (1:1) was added 70.2 mg thioglycerol (MW 92, 0.763 mmol). The mixture was stirred at room temperature for 20 h and was partitioned between ethyl acetate and water. The organic extracts were washed by saturated $NaHCO_3$ and saline respectively to neutral. After being dried by $MgSO_4$, the solution was concentrated and chromatographed to give 147 mg32 (78.3%) as yellow gum: IR(KBr) 3385, 2908, 1658, 1586, 1495, 1284 cm$^{-1}$; $^1$H NMR (CDCl$_3$) δ0.72 (m, 1H), 1.09 (m, 1H), 1.26 (m, 1H), 1.36 (s, 3H), 1.49 (m, 1H), 2.10 (s, 3H), 2.16 (s, 3H), 2.65 (m, 3H), 3.81 (m, 5H), 4.03 (s, 1H), 7.10 (s, 1H); $^{13}$C NMR (CDCl$_3$) δ197.6, 159.6, 141.8, 138.2, 135.1, 130.4, 126.2, 76.1, 70.7, 70.6, 65.2, 37.6, 35.2, 35.1, 29.5, 29.4, 27.6, 16.3, 14.2, 13.1, 9.5; MS m/z 336 (M$^+$), 261, 229, 201; HRMS for $C_{18}H_{24}O_4S$ calcd 336.1395, found 336.1395; UV λmax (methanol) 332 nm (ε6893).

Compound 16. To the solution of 22 mg HMA (MW 246, 0.089 mmol) in 3 ml acetone and 1 M $H_2SO_4$ solution (1:1) was added 7.5 ml ethyl ether. The mixture was stirred at room temperature for 24 h and was partitioned between ethyl acetate and water. The organic extracts were washed by saturated $NaHCO_3$ and saline respectively to neutral. After being dried by $MgSO_4$, the solution was concentrated and chromatographed to give 17 mg 16 (80.2%) as yellow gum: IR (KBr) 3457, 2968, 1659, 1592, 1502, 1284, 1097 cm$^{-1}$; $^1$H NMR (CDCl$_3$) δ0.72 (m, 1H), 1.08 (m, 1H), 1.23 (t, J=6.9 Hz, 3H), 1.33 (m, 1H), 1.38 (s, 3H), 1.48 (m, 1H), 2.11 (s, 3H), 2.14 (s, 3H), 3.53 (q, J=6.9 Hz, 2H), 3.91 (s, 1H), 4.42 (q, $J_{AB}$=10.7, 2H), 7.10 (s, 1H); $^{13}$C NMR (CDCl$_3$) δ197.4, 159.5, 142.2, 138.8, 134.3, 130.0, 126.4, 75.8, 65.0, 63.5, 37.2, 27.2, 15.6, 14.8, 13.8, 12.7, 9.0; MS m/z 274 (M$^+$), 261, 228, 200, 185; HRMS for $C_{17}H_{22}O_3$ calcd 274.1569, found 274.1568; UV λmax (methanol) 330 rum (ε7225).

Compound 17. To the solution of 36 mg HMAF (MW 246, 0.146 mmol) in 3 ml acetone and 1 M $H_2SO_4$ solution (1:1) was added 0.5 ml ethyl ether. The mixture was stirred at room temperature for 30 h and was partitioned between ethyl acetate and water. The organic extracts were washed by saturated $NaHCO_3$ and saline respectively to neutral. After being dried by $MgSO_4$, the solution was concentrated and chromatographed to give 5 mg 17 (14.4%), 11 mg 16 and 13 mg HMA. 17 is a yellow gum: IR (KBr) 3433, 2920, 1659, 1592, 1502, 1350, 1163 cm$^{-1}$; $^1$H NMR (CDCl$_3$) δ0.67 (m, 1H), 1.08 (m, 1H), 1.31 (m, 1H), 1.37 (s, 3H), 1.48 (m, 1H), 2.07 (s, 3H), 2.11 (s, 3H), 4.48 (s, 2H), 7.10 (s, 1H); $^{13}$C NMR (CDCl$_3$) δ197.9, 159.9, 143.3, 139.1, 134.6, 129.6, 126.8, 76.1, 63.2, 37.6, 27.5, 15.9, 14.2, 13.1, 9.4; MS m/z 475 (M+H), 391, 307, 229; HRMS for $C_{30}H_{34}O_5$ (M+H) calcd 475.2535, found 475.2467; UV λmax (methanol) 330 nm (ε 12905).

Compound 18. To the solution of 1.5 g HMAF (MW 246, 6.098 mmol) in 66 ml acetone and 40 ml 1 M $H_2SO_4$ solution (1:1) was added 20 g fructose. The mixture was stirred at room temperature for overnight and was partitioned between ethyl acetate and water. The organic extracts were washed by saturated $NaHCO_3$ and saline respectively to neutral. After being dried by $MgSO_4$, the solution was concentrated and chromatographed (use methylene chloride and methanol as solvents) to give 350 mg 18 (14.1%, mixture) as yellow gum (with 701 mg HMAF recycled); IR (KBr) 3397, 2932, 1659, 1574, 1369, 1085 cm$^{-1}$; MS m/z 409 (M+H), 307, 229, 203; HRMS for $C_{21}H_2O_8$ (M+H) calcd 409.1863, found 409.1869; UV; λmax (methanol) 332 nm (ε4745).

Compound 19. To the solution of 110 mg HMAF (MW 246, 0.447 mmol) in 15 ml acetone and 1 M $H_2SO_4$ solution (1:1) was added 5 ml glycerol. The mixture was stirred at room temperature for 22 h and was partitioned between ethyl acetate and water. The organic extracts were washed by saturated $NaHCO_3$ and saline respectively to neutral. After being dried by $MgSO_4$, the solution was concentrated and chromatographed (add 5% methanol to the normal solvent system) to give 79 mg 19 (55.2%) as yellow gum (with 40 mg HMAF recycled): IR (KBr) 3415, 2926, 1659, 1586, 1103 cm$^{-1}$; $^1$H NMR (CDCl$_3$) δ 0.72 (m, 1H), 1.08 (m, 1H), 1.26 (m, 1H), 1.37 (s, 3H), 1.50 (m, 1H), 2.10 (s, 3H), 2.15 (s, 3H), 2.57 (s, 1H), 3.58 (m, 4H), 3.86 (m, 1H), 3.91 (s, 1H), 4.51 (q, $J_{AB}$=12.9 Hz, 2H), 7.10 (s, 1H); $^{13}$C NMR (CDCl$_3$) δ198.0, 160.1, 143.2, 138.8, 134.6, 129.4, 126.9, 76.2, 70.9, 70.6, 64.4, 63.8, 37.6, 27.4, 16.1, 14.2, 13.1, 9.4; MS m/z 320 (M$^+$), 277, 228, 185; HRMS for $C_{18}H_{24}O_5$ calcd 320.1623, found 320.1616; UV λmax (methanol) 331 nm (ε7920).

Compound 20 & 53. To the solution of 188 mg HMAF (MW 246, 0.764 mmol) in 10 ml acetone and 1 M $H_2SO_4$ solution (1:1) was added 5 ml 2-bromoethanol. The mixture was stirred at room temperature for 4.5 h and was partitioned between ethyl acetate and water. The organic extracts were washed by saturated NaHCO$_3$ and saline respectively to neutral. After being dried by MgSO$_4$, the solution was concentrated and chromatographed to give 179.2 mg 20 (66.4%) as yellow gum: IR (KBr) 3445, 2914, 1650, 1592, 1502. 1097 cm$^{-1}$; $^1$H NMR (CDCl$_3$) δ0.71 (m, 1H), 1.07 (m, 1H), 1.35 (m, 1H), 1.38 (s, 3H), 1.48 (m, 1H), 2.15 (s, 3H), 3.47 (t, J=6.0 Hz, 2H), 3.77 (t, J=6.0 Hz, 2H), 3.91 (s, 1H), 4.54 (q, J$_{AB}$=12 Hz, 2H), 7.09 (s, 1H); $^{13}$C NMR (CDCl$_3$) δ198.1, 160.6, 143.2, 138.9, 134.4, 129.3, 127.0, 76.3, 69.4, 64.1, 37.7, 30.6, 27.6, 16.4, 14.3, 13.2, 9.5; MS m/z 352 (M–H), 326, 228, 285; HRMS for C$_{17}$H$_{21}$BrO$_3$ (M–H) calcd 352.0674, found 352.0671; UV λmax (methanol) 332 nm (ε7777). 53 was obtained as by product as a yellow gum: $^1$H NMR (CDCl$_3$) δ0.72 (m, 1H), 1.05 (m, 1H), 1.32 (m, 1H), 1.37 (s, 3H), 1.50 (m, 1H), 2.13 (s, 3H), 2.15 (s, 3H), 3.46 (t, J=6.3 Hz, 2H), 3.65 (m, 4H), 3.79 (t, J=6.3 Hz, 2H), 3.90 (s, 1H), 4.51 (q, J$_{AB}$=12 Hz, 2H), 7.09 (s, 1H).

Compound 21. To the solution of 260 mg HMAF (MW 246, 1.057 mmol) in 6 ml 2-methoxyl propene was added 2 drops POCl$_3$. The mixture was stirred at room temperature for 6 days and was partitioned between ethyl acetate and water. The organic extracts were washed by saturated NaHCO$_3$ and saline respectively to neutral. After being dried by MgSO$_4$, the solution was concentrated and chromatographed to give 133 mg 21 (39.6%) as yellow gum (with 87 mg HMAF recycled): IR (KBr) 3457, 2980, 1665, 1598, 1502, 1091 cm$^{-1}$, $^1$H NMR (CDCl$_3$) δ0.72 (m, 1H), 1.06 (m, 1H), 1.25 (m, 1H), 1.38 (s, 3H), 1.41, (s, 3H), 1.42 (s, 3H), 2.15 (s, 3H), 3.25 (s, 6H), 3.95 (s, 1H), 4.43 (s, 2H), 7.11 (s, 1H); $^{13}$C NMR (CDCl$_3$) δ197.7, 159.5, 142.2, 134.9, 134.8, 130.5, 126.7, 100.3, 76.1, 54.4, 48.6, 37.4, 27.5, 24.4, 24.3, 15.9, 14.0, 13.0, 9.3; MS m/z 318 (M$^+$), 260, 229, 185, 73; HRMS for C$_{19}$H$_{26}$O$_4$ calcd 318.1831, found 318.1823; UV λmax (methanol) 330 nm (ε8728).

Compound 22. To the solution of 9.0 mg HMAF (MW 246, 0.037 mmol) in 9 ml acetone and 1 M H$_2$SO$_4$ solution (1:1) was added 4.5 ml ethylene glycol. The mixture was stirred at room temperature for 2 h and was partitioned between ethyl acetate and water. The organic extracts were washed by saturated NaHCO$_3$ and saline respectively to neutral. After being dried by MgSO$_4$, the solution was concentrated and chromatographed to give 11 mg 22 (100%) as yellow gum: IR (KBr) 3439, 2914, 1665, 1598, 1508, 1344, 1103 cm$^{-1}$, $^1$H NMR (CDCl$_3$) δ0.71 (m, 1H), 1.06 (m, 1H), 1.32 (m, 1H), 1.36 (s, 3H), 1.47 (m, 1H), 2.11 (s, 3H), 2.14 (s, 3H), 2.55 (s, 1H), 3.57 (t, J=4.5 Hz, 2H), 3.73 (t, J=4.5 Hz, 2H), 3.98 (s, 1H), 4.50 (q, J$_{AB}$=12 Hz, 2H), 7.09 (s, 1H); $^{13}$C NMR (CDCl$_3$) δ197.9, 160.0, 142.9, 138.9, 134.5, 129.6, 126.8, 76.1, 70.9, 64.2, 61.6, 37.5, 27.4, 16.0, 14.1, 13.1, 9.3; MS m/z 290 (M$^+$), 250, 228, 185; HRMS for C$_{17}$H$_{22}$O$_4$ calcd 290.1518, found 190.1515; UV λmax (methanol) 331 nm (ε9404).

Compound 10 & 13. To the solution of 1 g fulvene (MW 216, 4.63 mmol) in 5 ml acetone and 2.5 ml 2 M H$_2$SO$_4$ solution was added 2.5 ml acrolein. The mixture was stirred at room temperature for 7 h and was partitioned between ethyl acetate and water. The organic extracts were washed by saturated NaHCO$_3$ and saline respectively to neutral. After being dried by MgSo$_4$, the solution was concentrated and chromatographed to give 378 mg 10 (30.0%) and 241 mg 13 (13.6%). 10 is a yellow gum: 0.68 (m, 1H), 1.07 (m, 1H), 1.32 (m, 1H), 1.36 (s, 3H), 1.46 (m, 1H), 2.01 (s, 3H), 2.06 (s, 3H), 2.65 (t, J=7.8 Hz, 2H), 3.00 (m, 2H), 3.93 (s, 1H), 7.12 (s, 1H), 9.83 (s, 1H); $^{13}$C NMR (CDCl$_3$) δ200.4, 196.3, 157.3, 139.4, 138.3, 135.4, 133.7, 125.3, 75.4, 43.5, 36.9, 27.0, 19.5, 15.4, 13.4, 12.4, 8.6; MS m/z 272 (M$^+$), 244, 215, 201; HRMS for C$_{17}$H$_{20}$O$_3$ calcd 272.1413, found 272.1416; UV λmax (methanol) 332 nm (ε8500). 13 is also a yellow gum (mixture): HRMS for C$_{23}$H$_{28}$O$_5$ calcd 384.1937, found 384.1947; UV λmax (methanol) 329 nm (ε6000).

Compound 30, 31 & 45. To the solution of 108 mg HMAF (MW 246, 0.439 mmol) in 40 ml acetone and THF (1:1) was added 1.5 ml methyl thioglycolate. The mixture was stirred at room temperature for 4 days and was partitioned between ethyl acetate and water. The organic extracts were dried by MgSO$_4$, concentrated and chromatographed to give 44 mg 30, 20 mg 31 and 29 mg 45. 30 is a yellow gum: $^1$H NMR (CDCl$_3$) δ0.70 (m, 1H), 1.09 (m, 1H), 1.33 (s, 3H), 1.35 (m, 1H), 1.50 (m, 1H), 2.14 (s, 3H), 2.15 (s, 3H), 3.23 (s, 2H), 3.67 (s, 3H), 3.74 (s, 3H), 3.92 (s, 2H), 4.08 (m, 3H); MS m/z 438 (M$^+$), 424, 333, 315; HRMS for C$_{21}$H$_{26}$O$_6$S$_2$ calcd 438.1172, found 438.1188; UV λmax (methanol) 372 nm (ε10760),243 nm (ε14364). 31 is a light yellow gum: $^1$H NMR (CDCl$_3$) δ0.46 (m, 1H), 0.88 (m, 1H), 1.04 (m, 1H), 1.32 (s, 3H), 1.38 (m, 1H), 1.87 (s, 3H), 2.03 (s, 3H), 3.13 (m, 2H), 3.44 (m, 3H), 3.73 (s, 3H), 3.77 (s, 3H), 4.02 (s, 1H), 4.41 (q, 2H); MS m/z 456 (M$^+$), 425, 351, 333; HRMS for C$_{21}$H$_{28}$O$_7$S$_2$ calcd 456.1277, found 456.1288; UV λmax (methanol) 263 nm (ε17264), 204 nm (ε8648). 45 is also a yellow gum: MS m/z 352 (M$^+$), 334, 263, 244, 229, 201; HRMS for C$_{18}$H$_{24}$O$_5$S calcd 352.1345, found 352.1333; UV λmax (methanol) 328 nm (ε2692), 238 nm (ε11099).

Compound 9. To the solution of 30 mg 10 (MW 272, 0.110 mmol) in 5 ml THF was added 5 drops HOAc and some sodium cyanoborohydride. The mixture was stirred at room temperature for 1 h and was partitioned between ethyl acetate and water. The organic extracts were washed by saturated NH$_4$Cl and saline respectively to neutral. After being dried by MgSO$_4$, the solution was concentrated and chromatographed to give 21 mg 9 (69.5%) as yellow gum: $^1$H NMR (CDCl$_3$) δ0.67 (m, 1H), 1.06 (m, 1H), 1.26 (m, 1H), 1.36 (s, 3H), 1.46 (m, 1H), 1.73 (m, 2H), 2.06 (s, 3H), 2.07 (s, 3H), 2.74 (m, 2H), 3.70 (t, J=6.3 Hz, 2H), 3.96 (s, 1H), 1.74 (s, 1H; $^{13}$C NMR (CDCl$_3$) δ197.0, 157.7, 139.6, 139.0, 136.6, 136.5, 128.2, 75.9, 62.0, 37.3, 33.0, 27.5, 24.0, 15.9, 13.8, 12.8, 9.0; MS m/z 274 (M$^+$), 246, 215, 187; HRMS or C$_{17}$H$_{22}$O$_3$ calcd 274.1569, found 274.1557; UV λmax (methanol) 330 nm (ε6700).

Compound 27. To the solution of 163 mg HMAF (MW 246, 0.663 mmol) in 10 ml methylene chloride was added 0.18 ml pyridine and 0.34 ml phenyl chloroformate at 0° C. under argon. The mixture was stirred for 3 h and was partitioned between ethyl acetate and water. The organic extracts were washed with saline. After being dried by MgSO$_4$, the solution was concentrated and chromatographed to give 20 mg 27 as yellow gum: $^1$H NMR (CDCl$_3$) δ0.85 (m, 1H), 1.18 (m, 1H), 1.43 (m, 1H), 1.52 (s, 3H), 1.61 (m, 1H), 2.12 (s, 3H), 2.28 (s, 3H), 4.04 (s, 1H), 5.06 (q, J$_{AB}$=11.1 Hz, 2H), 6.93–7.47 (m, 6H).

Compound 28. To the solution of 116 mg HMAF (MW 246, 0.447 mmol) in 10 ml methylene chloride was added 0.10 ml pyridine and 0.25 ml benzyl chloride under argon. The mixture was concentrated and chromatographed to give 152 mg 28 (92.1%) as yellow gum (with 13 mg HMAF recycled): $^1$H NMR (CDCl$_3$) δ0.65 (m, 1H), 1.02 (m, 1H), 1.18 (m, 1H), 1.32 (s, 3H), 1.44 (m, 1H), 2.03 (s, 3H), 2.16 (s, 3H), 3.86 (s, 1H), 5.28 (q, J$_{AB}$=13.2 Hz, 2H), 7.06 (s, 1H).

Figure 2A:
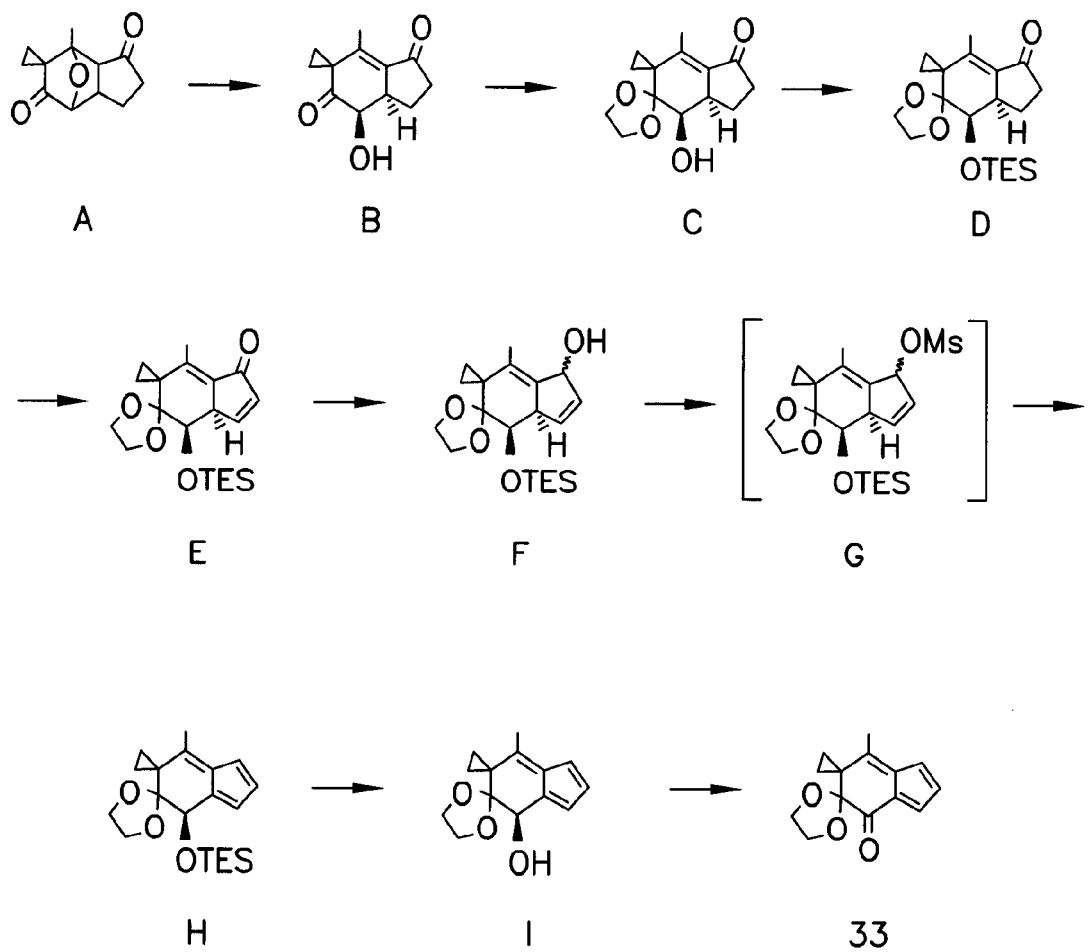
FIG. 2A is a schematic showing the synthesis of compound 33.

Compound 33. Compound 33 was made according to the schematic shown in FIG. 2A. Compound A was made following literature as a white solid: mp 134–6° C.; IR (KBr) 2993, 2952, 1757, 1743, 1454 cm$^{-1}$; $^1$H NMR (CDCl$_3$) d 0.74 (m, 1H), 1.03 (m, 1H), 1.13 (m, 1H), 1.25 (s, 3H), 1.32 (m, 1H), 2.08 (m, 2H), 2.27 (m, 2H), 2.54 (d, J=7.5 Hz, 1H), 2.92(m, 1H), 4.45 (s, 1H); $^{13}$C NMR (CDCl$_3$) d 216.6, 211.4, 87.7, 87.4, 57.6, 41.3, 39.2, 38.3, 25.1, 14.1, 13.4, 11.9; MS m/z 206 (M$^+$), 177, 149, 124; HRMS for C$_{12}$H$_{14}$O$_3$ calcd 206.0943, found 206.0941.

Compound B. To a stirred solution of A (2.83 g, 13.7 mmol) and 2-propanol (500 ml) was added K$_2$CO$_3$ (8 g, 58.0 mmol) at 25° C. The mixture was stirred for 7 days, then partitioned between EtOAc and water. The organic extract was washed with saturated NH$_4$Cl and dried over MgSO$_4$. Then the crude product was concentrated and chromatographed to give 1.88 g of A and 0.78 g of B (82.1%). B is a white solid: mp 183–5° C.; IR (KBr) 3369, 2995, 1696, 1616, 1407, 1367, 1226 cm$^{-1}$; $^1$H NMR (CDCl$_3$) d 1.24 (m, 1H), 1.38 (m, 1H), 1.68 (m, 1H), 1.88 (m, 1H), 2.00 (s, 3H), 2.16 (m, 2H), 2.46 (m, 2H), 3.21 (m, 1H), 4.06 (d, J=2.7 Hz, 1H); $^{13}$C NMR (CDCl$_3$) d 206.1, 204.8, 147.5, 128.0, 72.0, 42.2, 39.5, 32.1, 21.7, 19.4, 18.6, 11.7; MS m/z 206 (M$^+$), 177, 150, 147; HRMS for C$_{12}$H$_{14}$O$_3$ calcd 206.0943, found 206.0944.

Compound C. p-Tolunesulfonic acid (12 mg, 0.063 mmol) was added to a stirred solution of B (107 mg, 0.519 mmol) and ethylene glycol (3.04 g, 49 mmol) in benzene (10 ml) at 25° C. which was then stirred for 24 h. The mixture was partitioned between EtOAc and saturated NaHCO$_3$. The combined organic layers were washed with saline, dried over MgSO$_4$ and concentrated to an oil which was chromatographed to give 5 mg of B and 118 mg of C (95.3%) as colorless oil: IR (KBr) 3469, 2952, 2892, 1757, 1690, 1616, 1374, 1159, 1085 cm$^{-1}$; $^1$H NMR (CDCl$_3$) d 1.00 (m, 3H), 1.36 (m, 1H), 1.88 (d, J=2.7 Hz, 3H), 1.96 (m, 2H), 2.36 (m, 2H), 3.19 (t, J=3.9 Hz, 1H), 3.78 (t, J=3.9 Hz, 1H), 4.00 (m, 4H); $^{13}$C NMR (CDCl$_3$) d 205.4 148.3, 128.3, 108.9, 67.9, 65.6, 64.5, 41.9, 39.3, 26.8, 20. 8, 12.8, 11.5, 6.22; MS m/z 250 (M$^+$), 221, 193, 177; HRMS for C$_{14}$H$_{18}$O$_4$ calcd 250.1205, found 250.1201.

Compound D. To a stirred solution of C (8.0 mg, 0.032mmol) and pyridine (0.5 ml) was added TESCl (0.1 ml, 0.25 mmol) under N$_2$. The reaction mixture was stirred at 60° C. for 30 min and then concentrated to an oil. The crude product was purified by chromatography to give 13 mg of D (quantitative) as a colorless oil: IR (KBr) 2959, 2885, 1710, 1610, 1454, 1414, 1381, 1219 cm$^{-1}$; $^1$H NMR (CDCl$_3$) d 0.62 (q, J=7.8 Hz, 6H), 0.94 (m, 1 1H), 1.28 (m, 1H), 1.83 (m, 1H), 1.87 (d, J=2.4 Hz, 3H), 2.35 (m, 2H), 3.13 (m, 2H), 3.75 (d, J=3.3 Hz, 1H), 4.01 (m, 4H); $^{13}$C (CDCl$_3$) d 205.6, 148.8, 128.8, 109.5, 69.1, 65.3, 64.7, 43.3, 39.5, 27.4, 21.5, 12.9, 11.6, 6.8, 6.5, 4.8; MS m/z 364 (M$^+$), 336, 291, 219, 161; HRMS for C$_{20}$H$_{32}$O$_4$Si calcd 364.2070, found 364.2070.

Compound E. A solution of D (13 mg, 0.0357 mmol) and phenylseleninic anhydride (13 mg, 0.0361 mmol) in chlorobenzene (0.5 ml) was stirred at 95° C. for 0.5 h under N$_2$. The solution was then concentrated and chromatographed to give 4.9 mg of D and 7.0 mg of E (78.2%) as colorless oil: IR (KBr) 2959, 2878, 1716, 1683, 1622, 1454, 1381, 1213 cm$^{-1}$; $^1$H NMR (CDCl$_3$) d 0.54 (q, J=6.3 Hz, 6H), 0.89 (m, 10H), 1.27 (m, 2H), 1.57 (m, 1H), 1.93 (m, 3H), 3.79 (s, 1H), 4.00 (m, 4H), 6.30 (dd, J=2.4, 6 Hz, 1H), 7.28 (dd, J=2.1, 6 Hz, 1H); $^{13}$C NMR (CDCl$_3$) d 195.9, 154.7, 146.9, 137.7, 127.5, 109.5, 69.2, 65.5, 64.6, 47.4, 28.0, 12.8, 11.1, 7.1, 6.7, 5.0; MS m/z 362 (M$^+$), 333, 289, 187, 159, 87; HRMS for C$_{20}$H$_{30}$O$_4$Si calcd 362.1913, found 362.1919.

Compound I. To the solution of E (20 mg, 0.055 mmol) and CeCl$_3$·7H$_2$O (35 mg, 0.094 mmol) in MeOH (1 ml) was added NaBH$_4$ (excess). The mixture was stirred for 15 min at 25° C. and then more NaBH$_4$ was added. After 15 min of stirring the mixture was partitioned between Et$_2$O and saturated NH$_4$Cl. The ether extract was dried over MgSO$_4$ and concentrated to give crude product F as pale yellow oil.

To the solution of the above crude product F in CH$_2$Cl$_2$ (1 ml) was added Et$_3$N (20 ml, 0.143 mmol) and MsCl (20 ml, 0.258 mmol) respectively at 25° C. It was stirred for 5 min. Then the mixture was partitioned between Et$_2$O and saturated NaHCO$_3$. The ether extract was washed by saline and dried over MgSO$_4$. After concentration, it was chromatographed to give H and I as yellow gum.

To the solution of the above compound H in acetone (2 ml) and water (1 ml) was added some p-TsOH at room temperature. The mixture was set aside for 5 min and partitioned between Et$_2$O and saturated NaHCO$_3$. Then the ether extract was washed by saline and dried by MgSO$_4$. After concentration and chromatography, it was mixed with the above product I to give 10.5 mg of I as yellow gum: IR (KBr) 3456, 2912, 2885, 1730, 1636, 1441, 1367 cm$^{-1}$; $^1$H NMR (CDCl$_3$) d 0.75 (m, 1H), 1.10 (m, 2H), 1.24 (m, 1H), 1.88 (s, 3H), 2.34 (d, J=6.9 Hz, 1H), 3.95 (m, 2H), 4.06 (m, 2H), 4.68 (d, J=5.7 Hz, 1H), 6.34 (m, 1H), 6.42 (m, 2H); $^{13}$C NMR (CDCl$_3$), d 152.0, 139.8, 134.6, 130.5, 125.3, 117.9, 111.9, 71.3, 67.0, 66.1, 31.5, 16.4, 9.5, 6.6; MS m/z232 (M$^+$), 215, 189, 160, 145; HRMS for C$_{14}$H$_{16}$O$_3$ calcd 232.1099, found 232.1093.

Compound 33. A solution of 1 (7.3 mg, 31 mmol) and pyridinium dichromate (26 mg, 69 mmol) in CH$_2$Cl$_2$ (1 ml) was stirred for 1 h at 25° C. The mixture was diluted by Et$_2$O and then filtered. The concentrated crude product was chromatographed to give 5.2 mg of 33 (71.9%) as yellow crystal: mp 138–140° C.; IR (KBr) 2959, 2892, 1683, 1616, 1549, 1441, 1360 cm$^{-1}$; 1H NMR (CDCl$_3$) d 1.14 (m, 211), 1.35 (m, 2H), 2.06 (s, 31), 4.02 (m, 2H), 4.16 (m, 2H), 6.63 (dd, J=2.4, 4.8 Hz, 11), 6.76 (d, J=4.8 Hz, 1H), 7.39 (s, 1H); $^{13}$C NMR (CDCl$_3$) d 187.6, 159.6, 140.3, 135.4, 131.0, 127.9, 124.8, 106.2, 66.0, 33.4, 16.9, 12.9; MS m/z 230 (M$^+$), 202, 158; HRMS for C$_{14}$H$_{14}$O$_3$ calcd 230.0942, found 230.0948; UV 1$_{max}$ (methanol) 230 nm (e 6543), 330 (e 3484).

Figure 2B:
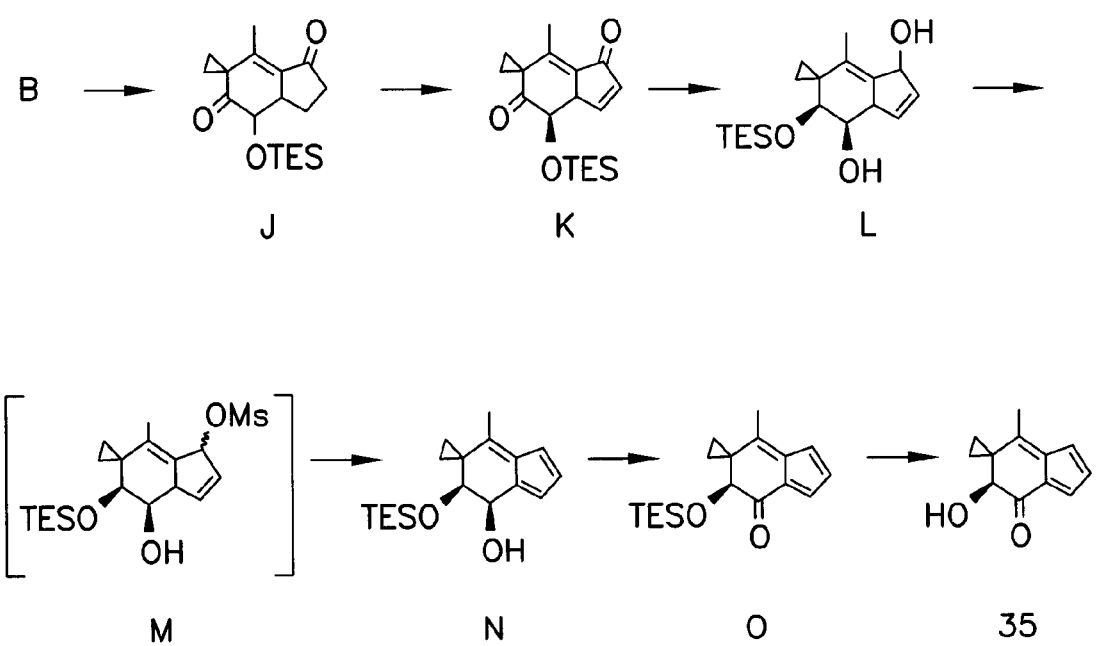
FIG. 2B is a schematic showing the synthesis of compound 35.

Compound 35. Compound 35 was made according to the schematic shown in FIG. 2B. Compound J. To a solution of B (37 mg, 0.18 mmol) in pyridine (3 ml) was added TESCl (0.25 ml, 0.624 mmol). The mixture was stirred at 60° C. for 0.5 h under N$_2$ After concentration and chromatography, it gave 50 mg of J (87%) as colorless oil: IR (KBr) 2952, 2872, 1703, 1622, 1461, 1414, 1226 cm$^{-1}$; $^1$H NMR (CDCl$_3$) d 0.58 (q, J=7.8 Hz, 6H), 0.97 (m, 10H), 1.25 (m, 2H), 1.58 (m, 1H), 1.85 (m, 2H), 1.98 (s, 3H), 2.42 (m, 2H), 3.09 (b, 1H), 4.01 (d, J=3 Hz, 1H); $^{13}$C NMR (CDCl$_3$) d 206.0, 205.0, 147.0, 128.6, 72.6, 43.0, 39.6, 32.1, 21.4, 19.6, 18.0, 11.5, 6.5, 4.5; MS m/z 320 (M$^+$), 291, 259, HRMS for C$_{18}$H$_{28}$O$_3$Si calcd 320.1808, found 320.1803.

Compound K. The solution of J (278 mg, 0.869 mmol) and phenylseleninic anhydride (320 mg, 0.889 mmol) in chlorobenzene (2.5 ml) was stirred at 95° C. for 0.5 h under N$_2$. The mixture was then concentrated and chromatographed to give 58.7 mg of J and 131.2 mg of K (60.2%) as colorless gum: IR (KBr) 2952, 2878, 1730, 1690, 1636, 1454, 1240 cm$^{-1}$; $^1$H NMR (CDCl$_3$) d 0.52 (q, J=7.8 Hz, 6H), 0.85 (t, J=7.8 Hz, 9H), 1.20 (m, 1H), 1.36 (m, 1H), 1.69 (m, 1H), 1.82 (m, 1H), 2.06 (s, 3H), 3.58 (s, 1H), 4.26 (d, J=2.4 Hz, 1H), 6.45 (dd, J=2.1 6 Hz, 1H), 7.33 (dd, J=2.1, 6 Hz, 1H); $^{13}$C NMR (CDCl$_3$) d 205.9, 195.3, 153.2, 144.3, 139.4, 127.7, 72.1, 47.3, 32.4, 20.1, 19.7, 11.4, 6.4, 4.4; MS m/z 318 (M$^+$), 289, 261; HRMS for C$_{18}$H$_{26}$O$_3$Si calcd 318.1651, found 318.1658.

Compound N. To a solution of K (9.5 mg, 0.0299 mmol), CeCl$_3$·7H$_2$O (58.5 mg, 0.157 mmol) in MeOH (0.3 ml) was added NaBH₄ (excess) at 25° C. It was stirred for 30 min. Then the mixture was partitioned between Et₂O and saturated NH₄Cl. The ether extract was dried by MgSO₄ and concentrated to give crude product L as pale yellow oil.

To the solution of above L in CH₂Cl₂ (0.2 ml) was added Et₃N (5 ml, 0.036 mmol) and MsCl (5 ml, 0.965 mmol) at 25° C. The mixture was stirred for 5 min and then separated between Et₂O and saturated NaHCO₃. Then the ether extract was washed by saline and dried by MgSO₄. After concentration, it was chromatographed to give 8.2 mg of N (90.3%) as yellow gum: IR (KBr) 3557, 3449, 2946, 2878, 1716, 1643, 1461, 1112 cm⁻¹; ¹H NMR (CDCl₃) d 0.66 (q, J=7.8 Hz, 6H), 0.87 (m, 2H), 0.98 (t, J=7.8 Hz, 9H), 1.26 (m, 2H), 1.86 (s, 1H), 2.55 (d, J=3.9 Hz, 1H), 3.24 (s, 1H), 4.94 (d, J=2.1 Hz, 1H), 6.35 (m, 2H), 6.46 (m, 1H),; ¹³C NMR (CDCl₃) d 148.9, 140.0, 130.4, 117.8, 117.5, 77.0, 68.6, 61.9, 16.1, 11.6, 7.8, 6.8, 5.0; MS m/z 304 (M⁺), 287, 275; HRMS for C₁₈H₂₈O₂Si calcd 304.1859, found 304.1860.

Compound O. A solution of N (1.2 mg, 3.95 mmol) and Dess-Martin reagent (2.2 mg, 5.19 mmol) in CH₂Cl₂ (0.2 ml) was stirred for 30 min at 25° C. The mixture was separated between Et₂O and 10% Na₂SO₃. Then the ether extract was washed by saline and dried by MgSO₄. After concentration, it was chromatographed to give 1.1 mg of O (92.3%) as yellow gum: IR (KBr) 2952, 2872, 1690, 1610, 1549, 1354, 1132 cm⁻¹; ¹H NMR (CDCl₃) d0.71 (q,J=7.8 Hz, 6H), 0.85 (m, 1H), 0.97 (t, J=7.8 Hz, 9H), 1.21 (m, 2H), 1.45 (m, 1H), 2.08 (s, 3H), 4.50 (s, 1H), 6.66 (dd, J=2.4, 4.8 Hz, 1H), 6.72 (d, J=5.1 Hz, 1H), 7.25 (s, 1H); ¹³C NMR (CDCl₃) d 193.3, 161.2, 140.7, 131.8, 131.2, 128.3, 122.8, 32.9, 17.1, 12.5, 10.3, 6.9, 5.2; MS m/z 302 (M⁺), 273, 245; HRMS for C₁₈H₂₆O₂Si calcd 302.1702, found 302.1710; UV $1_{max}$ 227 nm (e 15612), 323 nm (e 10720).

Compound 35. To a solution of O (9.0 mg, 0.0298 mmol) in acetone (0.8 ml) and H₂O (0.4 ml) was added some p-TsOH. The mixture was stirred for 30 min. Then it was partitioned between Et₂O and saturated NaHCO₃. The ether extract was washed by saline and dried by MgSO₄. After concentration, it was chromatographed to give quantitative 35 as yellow gum: IR (KBr) 3449, 3013, 2925, 1663, 1609, 1441, 1367, 1260 cm⁻¹; ¹H NMR (CDCl₃) d 0.81 (m, 1H), 1.25 (m, 1H), 1.36 (m, 1H), 1.44 (m, 1H), 2.12 (s, 3H), 3.82 (d, J 2.4 Hz, 1H), 4.55 (d, J=2.1 Hz, 1H), 6.70 (dd, J=2.7, 5.1 Hz, 1H), 6.81 (t, 1H), 7.32 (s, 1H); ¹³C NMR (CDCl₃) d 194.2 162.2, 140.9, 132.7, 131.4, 126.5, 124.1, 74.6, 32.8, 17.0, 12.7, 10.3; MS m/z 188 (M⁺), 160, 145; HRMS for C₁₂H₁₂O₂ calcd 188.0837, found 188.0840; UV $1_{max}$ (methanol) 227 nm (e 13626), 323nm (e 7474).

Compound 42, 43 & 44. To the solution of 340 mg HMAF (MW 246, 1.38 mmol) and 110 mg imidazole (MW 68, 1.62 mmol) in 4 ml DMF was added 0.7 ml triethylsilyl chloride (d 0.898, MW 360, 1.75 mmol). The mixture was stirred at room temperature for one and half an hour. The mixture was partitioned between ethyl ether and saturated NaHCO₃. The ether extract was then washed by saline and dried by MgSO₄. After filtration and concentration, it was chromatographed to give 90.3 mg 42, 30 mg 43 and 41.7 mg 44. 42 is a yellow gum: ¹H NMR (CDCl₃) δ0.74 (m, 10H), 0.94 (t, J=7.8 Hz, 6H), 1.08 m, 1H), 1.26 (m, 1H), 1.37 (s, 2H), 1.46 (m, 1H), 2.11 (s, 3H), 2.17 (s, 3H), 4.62 (s, 2H), 7.02 (s, 1H). 43 is a yellow gum: ¹H NMR (CDCl₃) δ0.62 (m, 10H), 0.94 (t, J=7.5 Hz, 6H), 1.06 (m, 1H), 1.34 (m, 1H), 1.38 (s, 3H), 1.47 (m, 1H), 2.12 (s, 3H), 2.18 (s, 3H), 3.92 (s, 1H), 4.63 (q, $J_{AB}$=12.6 Hz, 2H), 7.09 (s, 1H). 44 is also a yellow gum: ¹H NMR (CDCl₃) δ0.65 (m, 19H), 0.87 (t, J=7.8 Hz, 12H), 1.00 (m, 1H), 1.17 (m, 1H), 1.30 (d, 3H), 1.36 (m, 1H), 2.03 (d, 3H), 2.09 (s, 3H), 4.55 (q, 2H), 6.96 (s, 1H).

Compound 38. Compound 10 was oxidized by Jones Reagent to give 38 as yellow gum: ¹H NMR (CDCl₃) δ0.69 (m, 1H), 0.88 (m, 1H), 1.05 (m, 1H), 1.36 (s, 3H), 1.47 (m, 1H), 2.06 (s, 3H), 2.07 (s, 3H), 2.52 (m, 2H), 3.03 (m, 2H), 7.13 (s, 1H).

Compound 46. 46 was obtained as a by product as a yellow gum when 10 was reduced to 9: ¹H NMR (CDC₃) δ0.68 (m, 1H), 1.06 (m, 1H), 1.25 (m, 1H), 1.36 (s, 3H), 1.47 (m, 1H), 2.04 (s, 3H), 2.05 (s, 3H), 2.06 (s, 3H), 2.27 (m, 2H), 2.72 (m, 2H), 3.95 (s, 1H), 4.10 (m, 2H), 7.13 (s, 1H).

Compound 39. 39 was obtained in small quantity when compound 10 was treated with sodium borohydride in methanol. 39 is a yellow gum: ¹H NMR (CDCl₃) δ0.67 (m, 1H), 1.06 (m, 1H), 1.32 (m, 1H), 1.36 (s, 3H), 1.46 (m, 1H), 1.78 (m, 2H), 2.05 (s, 3H), 2.70 (m, 2H), 3.33 (s, 3H), 3.34 (s, 3H), 3.95 (s, 111), 4.35 (t, J=2.4 Hz, 1H), 7.14 (s, 1H).

Compound 40. 40 was obtained in small quantity when compound 10 was treated with sodium borohydride in ethanol. 40 is a yellow gum: ¹H NMR (CDCl₃) δ0.67 (m, 1H), 1.04 (m, 1H), 1.21 (m, 6H), 1.29 (m, 1H), 1.36 (s, 3H), 1.46 (m, 1H), 1.77 (m, 2H), 2.05 (s, 3H), 2.06 (s, 3H), 2.71 (m, 2H), 3.50 (q, 2H), 3.65 (q, 2H), 3.95 (s, 1H), 4.48 (t, J=5.4 Hz, 2H), 7.13 (s, 1H).

Compound 15. When HMAF was treated with BF₃.Et₂O in acetic anhydride at −78° C., 15 was obtained in low yield as a yellow gum: ¹H NMR (CDCl₃) δ0.97 (m, 1H), 1.16 (m, 2H), 1.46 (m, 1H), 1.51 (s, 3H), 2.10 (s, 3H), 2.14 (s, 3H), 2.19 (s, 3H), 4.60 (s, 1H), 4.65 (s, 2H), 7.18 (s, 1H).

Compound 47. 47 was obtained as by product when HMAF was treated with acronitrile in sulfuric acid and acetone. 47 is a yellow gum: MS m/z 432 (M⁺), 414, 399, 386, 371, 217; HRMS for C₂₈H₃₂O₄ calcd 432.2302, found 432.2312.

Compound 48. 48 was formed as a by product when limited thio compound was used to make 26. 48 is a yellow gum: ¹H NMR (CDCl₃) δ0.64 (m, 1H), 1.05 (m, 1H), 1.26 (m, 1H), 1.37 (s, 3H), 1.48 (m, 1H), 1.84 (s, 3H), 2.16 (s, 3H), 2.28 (s, 3H), 2.32 (s, 3H), 4.04 (s, 2H), 6.87–7.27 (m, 8H); HRMS for C₂₈H₂₈O₂S₂ calcd 460.1532, found 160.1504.

Compound 49 & 50. To a solution of acylfulvene in acetone and 1 M H₂SO₄ solution (1:1) was added p-thiocresol at room temperature. The mixture was stirred for overnight and partitioned between EtOAc and water. The organic extracts were washed by saturated NaHCO₃ and saline respectively. After being dried by MgSO₄, it was concentrated and chromatographed to give 49 and 50 in low yield. 49 is a yellow gum: ¹H NMR (CDCl₃) δ0.69 (m, 1H), 0.88 (m, 1H), 1.06 (m, 1H), 1.25 (m, 1H), 1.37 (s, 3H), 2.16 (s, 3H), 2.22 (s, 3H), 2.28 (s, 3H), 3.90 (s, 1H), 6.90–7.30 (m, 5H). 50 is also a yellow gum: ¹H NMR (CDCl₃) δ0.63 (m, 1H), 1.06 (m, 1H), 1.25 (m, 1H), 1.37 (s, 3H), 1.45 (m, 1H), 1.83 (s, 3H), 2.16 (s, 3H), 2.28 (s, 3H), 2.32 (s, 3H), 4.04 (s, 1H), 6.87–7.30 (m, 8H).

Compound 41. When HMAF was treated with propargyl aldehyde in acetone and 1 M H₂SO₄ (1:1), 41 was obtained as a yellow gum: ¹H NMR (CDCl₃) δ0.72 (m, 1H), 1.14 (m, 1H), 1.31 (m, 1H), 1.38 (s, 3H), 1.42 (m, 1H), 2.05 (s, 3H), 2.13 (s, 3H), 3.96 (s, 1H), 6.55 (s, 1H), 7.16 (s, 1H), 7.17 (s, 1H), 9.68 (d, 1H).

Compound 54. 54 was obtained as by product when HMAF was prepared as a yellow gum: ¹H NMR (CDCl₃) δ0.67 (m, 2H), 1.01 (m, 2H), 1.22 (m, 2H), 1.34 (s, 3H), 1.48 (m, 2H), 1.71 (s, 3H), 1.79 (s, 3H), 2.04 (s, 3H), 2.18 (s, 3H), 3.86–4.21 (m, 4H), 4.60 (s, 2H), 7.15 (s, 1H).

Compound 55. 55 was obtained as by product when 23 was formed. 55 is a yellow gum: ¹H NMR (CDCl₃) δ1.70 (s, 3H), 2.29 (s, 3H), 2.37 (s, 3H), 2.95 (t, 3H), 3.74 (t, 3H), 4.22 (s, 1H), 4.91 (s, 2H), 6.40–7.15 (m, 8H).

Compound 36. HMAF was treated with imidazole in THF at room temperature to give 36 as a yellow gum: $^1$H NMR (CD$_3$OD) δ0.65 (m, 1H), 1.06 (m, 1H), 1.23 (m, 1H), 1.34 (s, 3H), 1.49 (m, 1H), 1.74 (s, 3H), 2.05 (s, 3H), 5.08 (d, 2H), 6.78–7.47 (m, 4H).

Compound 51 & 52. To a solution of HMAF in acetone and 1M H$_2$SO$_4$ (1:1) was added limited glycol dimercaptoacetate at room temperature. The mixture was stirred for several hours and worked up as usual to give 51 as a yellow gum: $^1$H NMR (CDCl$_3$) δ0.72 (m, 1H), 1.09 (m, 1H), 1.35 (m, 1H), 1.36 (s, 3H), 1.50 (m, 1H), 2.12 (s, 3H), 2.15 (s, 3H), 3.28 (t, JU=7.8 Hz, 4H), 3.87 (s, 1H), 3.92 (q, J$_{AB}$=13.2, 2H), 4.36 (s, 4H), 7.08 (s, 1H). 52 is also a yellow gum: $^1$H NMR (CDCl$_3$) δ0.72 (m, 2H), 1.10 (m, 2H), 1.37 (s, 6H), 1.53 (m, 2H), 2.14 (s, 6H), 2.19 (s, 6H), 3.25 (m, 4H), 3.87 (s, 2H), 4.37 (m, 4H), 4.65 (s, 4H), 7.09 (s, 2H).

Compound 37. To a solution of HMAF in acetone and 1M H$_2$SO$_4$ solution (1:1) was 1 added equivalent cysteine. The mixture was stirred at room temperature for overnight. Large amount of EtOAc was introduced and the aqueous layer was removed by adding MgSO$_4$. Solid NaHCO$_3$ was also added in order to neutralize the sulfuric acid. The solution was then filtered, concentrated and chromatographed to give 37 as a yellow gum: 1H NMR (CD$_3$OD) δ8 0.78 (m, 1H), 0.89 (m, 1H), 1.06 (m, 1H), 1.31 (s, 3H), 1.43 (m, 1H), 2.15 (s, 3H), 2.21 (s, 3H), 2.91–4.02 (m, 8H), 7.04 (s, 1H).

Compounds 56, 57 & 58. To a solution of HMAF in acetone and 1M H$_2$SO$_4$ (1:1) was added equivalent p-hydroxy thiophenol. The mixture was stirred at room temperature for overnight. The mixture was extracted by EtOAc. Then the organic extracts were washed by saturated NaHCO$_3$ and saline respectively. After being dried over MgSO$_4$, the solution was concentrated and chromatographed to give 56, 57 & 58. 56 is a yellow gum: $^1$H NMR (CDCl$_3$) 0.70 (m, 1H), 0.89 (m, 1H), 1.05 (m, 1H), 1.36 (s, 3H), 1.51 (m, 1H), 2.16 (s, 3H), 2.21 (s, 3H), 3.92 (s, 1H), 6.74 (d, J=8.4 Hz, 1H), 6.94 (d, J=8.4 Hz, 1H), 7.25 (s, 1H); 57 is a yellow gum: 0.67 (m, 1H), 1.07 (m, 1H), 1.24 (m, 1H), 1.37 (s, 3H), 1.51 (m, 1H), 1.67 (s, 3H), 1.95 (s, 3H), 4.08 (s, 1H), 6.45 (s, 1H), 6.78 (d, J=8.4 Hz, 1H), 7.33 (d, J=8.4 Hz, 1H); 58 is also a yellow gum: δ0.62 (m, 1H), 1.04 (m, 1H), 1.24 (m, 1H), 1.34 (s, 3H), 1.47 (m, 1H), 1.79 (s, 3H), 2.15 (s, 3H), 4.07 (s, 1H), 6.72 (d, J=8.4 Hz, 1H), 6.77 (d, J=8.4 Hz, 1H), 6.88 (d, J=8.4 Hz, 1H), 7.26 (d, J=8.4 Hz, 1H).

Example II

In Vitro Studies

To assess cytotoxic effects, various concentrations of illudins were added to cultures of MV522 (human lung carcinoma cell line) and 8392 (B-cell leukemia/lymphoma) cells for 48 hours, then cell growth/viability was determined by trypan blue exclusion. As an alternative to 48 hour continuous exposure studies, cells were plated in liquid culture in 96 well plates, exposed to various concentrations of illudins for 2 hours, pulsed with [$^3$H]-thymidine for one to two hours and harvested onto glass filters. The filter papers were added to vials containing scintillation fluid and residual radioactivity determined in a beta (scintillation) counter.

| Com- | 2 hour IC$_{50}$ (nm/l) | | 48 hour IC$_{50}$ (nm/l) | |
| --- | --- | --- | --- | --- |
| pound | MV522 | 8392 | MV522 | 8392 |
| 8 | 870 ± 90 | 12200 ± 740 | 630 ± 80 | 15100 ± 2200 |
| 9 | 500 ± 33 | 47100 ± 10950 | 850 ± 180 | 15100 ± 2200 |
| 10 | 8900 ± 1500 | 29400 ± 1600 | 165 ± 55 | 14450 ± 1650 |
| 13 | 5120 ± 650 | 11900 ± 1300 | 270 ± 130 | 4200 ± 400 |
| 11 | 4900 ± 900 | >100000 | 1200$^a$ | 40400 ± 6700 |
| 14 | 115 ± 30 | 9650 ± 1200 | 460 ± 120 | 1100 ± 250 |
| 21 | 2400 ± 940 | 34300 ± 9400 | 930 ± 250 | NT |
| 22 | 660 ± 180 | 31700 ± 1400 | 680 ± 180 | NT |
| 23 | 2920 ± 1140 | 138200 ± 13000 | 2750 ± 510 | NT |
| 24 | 1780 ± 200 | 12780 ± 2140 | 1210 ± 260 | NT |
| 25 | 1300 ± 310 | >25 μm/l | 1180 ± 120 | NT |
| 32 | 595 ± 185 | >50 μm/l | 205 ± 30 | NT |
| 33 | >4000 | 29900 ± 3300 | 4600 ± 200 | NT |

$^a$N = 2 due to instability

As shown above, the illudin analogs 8–33 are potent anti-tumor agents.

Example III

In Vivo Studies

Several analogs were chosen for in vivo studies. The anticancer agent mitomycin C was used as pharmaceutical control. Drug therapy was started 10 days after inoculation on a daily basis via IP route for 5 consecutive days. The animals were monitored for 3 weeks after start of therapy. With regard to all analogs administered, the maximum tolerated dose (MTD) was not achieved.

BALB/c nu/nu 4-week old female mice weighing 18–22 g were obtained from Simonsen, Inc. (Gilroy, Calif.) and maintained in the athymic mouse colony of the University of California (San Diego, Calif.) under pathogen free conditions using HEPA filter hoods. Animals were provided with sterilized food and water ad libitum in groups of 5 in plastic cages vented with polyester fiber filter covers. Clean, sterilized gowns, glove, face masks, and shoe and hood covers were worn by all personnel handling the animals. All studies were conducted in accordance with guidelines of the NIH "Guide for Care and Use of Animals" and approved by the University Institutional Animal Care and Use Committee (Protocol 3-006-2)

The MV522 lung carcinoma line used for xenograft studies was derived as described by Kelner et al. (*Anticancer Res.*, 15: 867–872; 873–878 (1995)) and maintained in antibiotic-free RPMI 1640 (Mediatech, Hermdon, Va.) supplemented with 10% fetal bovine serum and 2 mM glutamine in 37° C. humidified carbon dioxide incubator.

Mice were randomized into treatment groups of five animals each for initial studies and groups of 16–20 animals for confirming analogue efficacy. Each animal was earmarked and followed individually throughout the experiments. Mice received s.c. injections of the parental cell line MV522 using 10 million cells/inoculation over the shoulder. Ten days after s.c. implantation of the MV522 cells, when s.c. tumors were approximately 3×3 mm in size, animals received the desired drug and dosage. The effect of the drug on life span was calculated from median survival.

Although MV522 cells kill mice by metastases, primary s.c. tumor growth over the shoulder was monitored starting on the first day of treatment and at weekly intervals thereafter. Tumor size was measured in two perpendicular diameters. Tumor weights were estimated according to the formula w=(width)²×length/2). Relative weights (RW) were calculated to standardized variability in tumor size among test groups at initiation of treatment using the formula RW=Wt/wi, where Wi is the tumor weight for a given animal at beginning of drug treatment and Wt is tumor weight at a subsequent time. Animals were necropsied, and organs were examined for evidence of metastases.

Comparison of survival curves between groups of animals was by the method of Kaplan and Meir. For comparison of relative tumor weights between multiple groups of animals, ordinary ANOVA followed by Tukey-Kramer multiple Comparison post ANOVA analysis was performed (Kelner et al. (*Anticancer Res.*, 15: 867–872; 873–878 (1995)). Probability values (p) less than 0.05 were considered statistically significant.

| Compound | dose (mg/kg) | p value (tumor weight) |
|---|---|---|
| HMAF | 6 | <0.01 |
|  | 8 | <0.01 |
|  | 10 | <0.001 |
| 9 | 4 | <0.001 |
|  | 8 | <0.001 |
|  | 16 | <0.001 |
| 10 | 3 | <0.001 |
|  | 6 | <0.001 |
| 11 | 1.2 | <0.001 |
| 12 | 3.75 | <0.001 |
|  | 7.5 | <0.001 |
| 16 | 4 | <0.001 |
|  | 8 | <0.01 |
|  | 16 | <0.01 |
| 18 | 18 | <0.001 |
|  | 20 | <0.001 |
|  | 24 | <0.001 |
|  | 32 | <0.001 |
| 19 | 4 | <0.05 |
|  | 8 | <0.001 (toxic) |
|  | 16 | <0.001 (toxic) |
| 21 | 4 | <0.01 |
|  | 8 | <0.001 |
|  | 16 | <0.001 |
| 22 | 4 | <0.001 |
|  | 8 | <0.001 |
|  | 16 | toxic |
| 23 | 4 | <0.001 |
|  | 8 | <0.001 |
|  | 16 | <0.001 |
| 24 | 0.2 | <0.001 |
| 25 | 4 | <0.001 |
|  | 8 | <0.001 |
|  | 16 | <0.001 |
| 26 | 0.4 | <0.001 |
| 29 | 4 | <0.001 |
|  | 8 | <0.001 |
|  | 16 | <0.001 |
| 32 | 4 | <0.05 |
|  | 8 | >0.05 |
|  | 16 | <0.001 |
|  | 20 | <0.001 |
|  | 24 | <0.001 |
| 33 | 4 | <0.01 |
|  | 8 | <0.01 |
|  | 16 | <0.05 |
| mitomycin C | 1.6 | >0.05 |
|  | 2.0 | toxic |

Analog 21 appears to be more efficacious than HMAF, particularly in view of the fact that MTD was not achieved. Analogs 16, 32 and 33 were also effective. The high dose mitomycin C had an effect on tumor size. The dose, however, was toxic as all animals eventually succumbed before day 31. The low dose mytomycin C had little effect.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula (I):

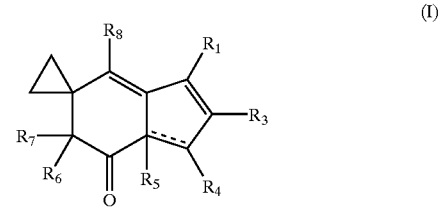

wherein $R_1$ is $(CH_2)n—(X)—(Y)$; n is 0–4, X is O or S or NH, and Y is an amino acid residue;

$R_3$ is H or $(C_1-C_4)$alkyl;

$R_4$ is H, $SCH_2CO_2(C_1-C_4)$alkyl, $O—(C_5-C_{12})$aryl or $S—(C_5-C_{12})$aryl where aryl is optionally substituted with halo, OH or $(C_1-C_4)$alkyl;

$R_5$ is H, OH or absent;

$R_6$ is $(C_1-C_4)$alkyl or H; and $R_7$ is OH or $Si((C_1-C_4)alkyl)_3$; or $R_6$ and $R_7$ together are ethylenedioxy;

$R_8$ is $(C_1-C_4)$alkyl, optionally substituted with OH or halo; the bond represented by - - - - is present or absent; or the pharmaceutically acceptable salts thereof.

2. A compound of claim 1, wherein n is 1, the bond represented by ---- is present, and $R_5$ is absent.

3. A compound of claim 2, wherein $R_3$ is $CH_3$, $R_4$ is H, $R_6$ is $CH_3$, $R_7$ is OH and $R_8$ is $CH_3$.

4. A compound of claim 3, wherein the amino acid residue is derived from glycine, alanine, cysteine or an analog thereof.

5. A compound of claim 4, wherein the amino acid residue is derived from glycine.

6. A compound of claim 4, wherein the amino acid residue is derived from alanine.

7. A compound of claim 4, wherein the amino acid residue is derived from cysteine.

* * * * *

UNITED STATES PATENT AND TRADEMARK OFFICE
CERTIFICATE OF CORRECTION

PATENT NO.    : 6,639,105 B2
DATED         : October 28, 2003
INVENTOR(S)   : Michael J. Kelner and Trevor C. McMorris It is certified that error appears in the above-identified patent and that said Letters Patent is hereby corrected as shown below:

Column 3,
Line 56, delete "AYE" and insert -- vivo -- therefor.

Column 4,
Line 3, delete "leukemiallymphomas" and insert -- leukemia/lymphomas -- therefor.
Line 27, delete "v" and insert -- vivo -- therefor --.
Line 57, delete "$CH_2C(O)$-O-$(C_2)_2$-O-$C(O)CH_2SH$" and insert
-- $CH_2C(O)$-O-$(CH_2)_2$-O-$C(O)CH_2SH$ -- therefor.

Column 6,
Lines 2 and 10, delete "(1)" and insert -- (I) -- therefor.

Column 9,
Line 63, delete "244$M^+$)" and insert -- 244 ($M^+$) -- therefor.

Column 10,
Line 11, delete "," after "6.97 (s,1H)" and insert -- ; -- therefor.
Line 30, insert -- , -- after "80.3".

Column 11,
Line 13, delete "8 0.72" and insert -- $\delta$0.72 -- therefor.
Line 21, insert -- (s, 3H), -- after "2.16".
Line 62, delete "HMA" and insert -- HMAF -- therefor.

Column 12,
Line 11, delete "rum" and insert -- nm -- therefor.
Line 42, delete ";" after "UV".
Line 54, delete "8 0.72" and insert -- $\delta$0.72 -- therefor.

Column 13,
Line 29, insert -- 1.49 (m, 1H), -- before "2.15".

Column 14,
Line 37, delete "1.74 (s, 1H" and insert -- 7.14 (s, 1H) -- therefor.
Line 40, delete "or" and insert -- for -- therefor.

Column 15,
Line 33, insert -- , -- after "205.4.".

UNITED STATES PATENT AND TRADEMARK OFFICE
CERTIFICATE OF CORRECTION

PATENT NO. : 6,639,105 B2
DATED : October 28, 2003
INVENTOR(S) : Michael J. Kelner and Trevor C. McMorris It is certified that error appears in the above-identified patent and that said Letters Patent is hereby corrected as shown below:

Column 16,
Line 26, delete "1" and insert -- I -- therefor.
Line 32, delete "1H" and insert -- $^1$H -- therefor.
Line 32, delete "(m,211)" and insert -- (m, 2H) -- therefor.
Line 33, delete "(s, 31)" and insert -- (s, 3H) -- therefor.
Lines 33-34, delete "(dd, J=2.4, 4.8 Hz, 11)" and insert -- (dd, J=2.4, 4.8 Hz, 1H) -- therefor.
Line 43, insert -- . -- after "$N_2$".
Line 61, insert -- , -- after "J=2.1".

Column 17,
Line 14, delete "(s, 1H)" after "1.86" and insert -- (s, 3H) -- therefor.
Line 15, delete "," after "6.46 (m, 1H)".
Line 43, insert -- = -- between "J" and "2.4 Hz,".
Line 45, insert -- , -- after "194.2".
Line 59, delete "1.08 m, 1H)" and insert -- 1.08 (m, 1H) -- therefor.

Column 18,
Line 7, delete "(CDC3)" and insert -- $CDCl_3$) -- therefor.
Line 14, insert -- 2.06 (s, 3H) -- after "2.05 (s, 3H)".

Column 19,
Line 15, delete "U" before "=7.8 Hz".
Line 15, insert -- Hz -- after "13.2".
Line 28, delete "1H" after "gum:" and insert -- $^1$H -- therefor.
Line 28, delete "δ8 0.78" and insert -- δ0.78 -- therefor.
Line 40, delete "0.70" and insert -- δ0.70 -- therefor.

UNITED STATES PATENT AND TRADEMARK OFFICE
CERTIFICATE OF CORRECTION

PATENT NO. : 6,639,105 B2
DATED : October 28, 2003
INVENTOR(S) : Michael J. Kelner and Trevor C. McMorris It is certified that error appears in the above-identified patent and that said Letters Patent is hereby corrected as shown below:

<u>Column 19 (cont'd),</u>
Line 43, delete "0.67" and insert -- δ0.67 -- therefor.

Signed and Sealed this

Twentieth Day of April, 2004

JON W. DUDAS
*Acting Director of the United States Patent and Trademark Office*